US006638980B1

(12) United States Patent
Su et al.

(10) Patent No.: US 6,638,980 B1
(45) Date of Patent: Oct. 28, 2003

(54) INHIBITORS OF FACTOR XA

(75) Inventors: Ting Su, Belmont, CA (US); Bing-Yan Zhu, Belmont, CA (US); Kim Kane-Maguire, Belmont, CA (US); Robert M. Scarborough, Half Moon Bay, CA (US); Penglie Zhang, San Francisco, CA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/576,633

(22) Filed: May 24, 2000

Related U.S. Application Data
(60) Provisional application No. 60/135,849, filed on May 24, 1999.

(51) Int. Cl.⁷ .................... A61K 31/165; C07C 229/04
(52) U.S. Cl. .................... 514/620; 514/617; 564/164; 564/182; 564/184
(58) Field of Search .................... 564/184, 182, 564/164; 514/617, 620

(56) References Cited

U.S. PATENT DOCUMENTS

| 3,235,597 A | 2/1966 | Mills et al. ............... 260/570.5 |
| 3,895,010 A | 7/1975 | Goralski et al. ......... 260/247.1 |

FOREIGN PATENT DOCUMENTS

| DE | 1 062 253 B | | 7/1959 |
| EP | 976722 | * | 2/2000 |
| EP | 1 020 434 A1 | | 7/2000 |
| WO | 98/28269 | | 7/1998 |
| WO | 98/28282 | | 7/1998 |
| WO | 98/31661 | * | 7/1998 |
| WO | 98/57934 | | 12/1998 |
| WO | 99/10316 | | 3/1999 |

OTHER PUBLICATIONS

Blicke, F.F., et al., "The Reaction Of The Chloromagnesium Devivative Of Chloromagnesium Phenylacetate With Isocyananes. Carbarny Chlorides And Isothiocyanates," *Journal of the American Chemical Society*, vol. 77, No. 18, pp. 4849–4851 (1955).

Saito, Toshinori, et al., "Traosacylation of Cephzlosporin; Isolation and Reactions of the Inudare Esters," *J.C.S. Perkin Transactions J*, No. 4, pp. 1058–1063 (1981).

Barrett, Anthony G. M., et al., "Phenol Oxidation and Biosynthesis Part 26. Isonitriles in the Synthesis of Benzylisoqumoline Derivatives," *J.C.S. Perkin Transactions J*, No. 3, pp. 652–661 (1979).

Nicholas, H. O. and Erickson. J. L. E. "Substituted Amides. L. The Preparation of Substituted Acctantides and the Corresponding Primary Amines," *Journal of the American Chemical Society*. vol. 48, No. 8, pp. 2174–2176 (1926).

Gray, Nancy M., et al., "Phencyclidine–like Effects of Tetrahydroisoquinolines and Related Compounds," *J. Med. Chem.*, vol. 32, No. 4, pp. 1242–1248 (1989).

Karaoka, Tadashi, et al., "Preparation of Sulfonamides From Sodium Sulfonates: $Ph_3PeBr_2$ and $P_3p-Cl_2$ as a Mild Halogenaring Reagent for Sulfonyl Bromides and Sulfonyl Chlorides," *SynthesisNo. 4*, pp. 423–426 (1998).

A. M. Istnaicl, et al., "2–(1–Naphthyioxy) Ethylamines With Enhanced Affinity For Human $5-HT_1Dbeta$ ($h5-HT_{1B}$) Scrontonin Receptors" *Journal of Medicnal Chemistry*, vol. 40, No. 26. pp. 4415–4419 (1997).

D. H. R. Barton et al., "The Catalytic Effect Of Copper Ions In The Phenylation Reaction Of David and Thieffry", *Journal of the Chemical Society, Chemical Communications*, No. 1, pp. 65–66 (1986).

L. W. Deady, et al., "A New Synthesis Of N–arylazetidines", *Tetrahedron Letters*, No. 14, pp. 1773–1776 (1968).

G.F. Grillot, et al., "Condensation of Thiophenois and Formaldehyde With Some Aromatic Amines", *Journal of Organic Chemsitry*, vol. 24, No. 8, pp. 1035–1038 (1959).

E. Bäder, et al., "Ncuc Methoden zur Darstcllung von Sulfonamincn (IV. Mittell.: Ploymerisationen und Polymer-isarionskatalysetoren)", *Chemische Berichte*, vol. 88, No. 1, pp. 41–49 (1955).

S. T. McDowell, et al., "Elimination–addition. Part XI. Electronic Effects Upon The Reactivity Of Aryl Vinyl Sulphones Towards Amines", *Journal of the Chemical Society, Section B: Physical Organic Chemistry*, No. 5, pp. 348–350 (1967).

A. W. M. Lee, et al., "A Facile Total Synthesis Of Isoquinoline Alkaloids", *Journal of the Chemical Society, Perkin Transactions J*, No. 3, pp. 309–310 (1992).

J. L. Bellerire, et al., "A Useful Approach To Primary Amines", *Synthetic Communications*, vol. 18, No. 1, pp. 29–36 (1988).

* cited by examiner

*Primary Examiner*—Zinna Northington Davis
(74) *Attorney, Agent, or Firm*—Townsend and Townsend and Crew LLP

(57) ABSTRACT

Novel compounds, their salts and compositions related thereto having activity against mammalian factor Xa are disclosed. The compounds are useful in vitro or in vivo for preventing or treating coagulation disorders.

20 Claims, No Drawings

INHIBITORS OF FACTOR XA

RELATED APPLICATIONS

This application claims benefit of priority under 35 USC §119(e) to U.S. Provisional Application No. 60/135,849 filed on May 24, 1999, which is herein incorporated in its entirety by reference.

FIELD OF THE INVENTION

This invention relates to novel compounds which are potent and highly selective inhibitors of isolated factor Xa or when assembled in the prothrombinase complex. These compounds show selectivity for factor Xa versus other proteases of the coagulation (e.g. thrombin, fVIIa, fIXa) or the fibrinolytic cascades (e.g. plasminogen activators, plasmin). In another aspect, the present invention relates to novel monoamidino-containing compounds, their pharmaceutically acceptable salts, and pharmaceutically acceptable compositions thereof which are useful as potent and specific inhibitors of blood coagulation in mammals. In yet another aspect, the invention relates to methods for using these inhibitors as therapeutic agents for disease states in mammals characterized by coagulation disorders.

BACKGROUND OF THE INVENTION

Hemostasis, the control of bleeding, occurs by surgical means, or by the physiological properties of vasoconstriction and coagulation. This invention is particularly concerned with blood coagulation and ways in which it assists in maintaining the integrity of mammalian circulation after injury, inflammation, disease, congenital defect, dysfunction or other disruption. Although platelets and blood coagulation are both involved in thrombus formation, certain components of the coagulation cascade are primarily responsible for the amplification or acceleration of the processes involved in platelet aggregation and fibrin deposition.

Thrombin is a key enzyme in the coagulation cascade as well as in hemostasis. Thrombin plays a central role in thrombosis through its ability to catalyze the conversion of fibrinogen into fibrin and through its potent platelet activation activity. Direct or indirect inhibition of thrombin activity has been the focus of a variety of recent anticoagulant strategies as reviewed by Claeson, G., "Synthetic Peptides and Peptidomimetics as Substrates and Inhibitors of Thrombin and Other Proteases in the Blood Coagulation System", Blood Coag. Fibrinol. 5, 411–436 (1994). Several classes of anticoagulants currently used in the clinic directly or indirectly affect thrombin (i.e. heparins, low-molecular weight heparins, heparin-like compounds and coumarins).

A prothrombinase complex, including Factor Xa (a serine protease, the activated form of its Factor X precursor and a member of the calcium ion binding, gamma carboxyglutamyl (Gla)-containing, vitamin K dependent, blood coagulation glycoprotein family), converts the zymogen prothrombin into the active procoagulant thrombin. Unlike thrombin, which acts on a variety of protein substrates as well as at a specific receptor, factor Xa appears to have a single physiologic substrate, namely prothrombin. Since one molecule of factor Xa may be able to generate up to 138 molecules of thrombin (Elodi et al., Thromb. Res. 15, 617–619 (1979)), direct inhibition of factor Xa as a way of indirectly inhibiting the formation of thrombin may be an efficient anticoagulant strategy. Therefore, it has been suggested that compounds which selectively inhibit factor Xa may be useful as in vitro diagnostic agents, or for therapeutic administration in certain thrombotic disorders, see e.g., WO 94/13693.

Polypeptides derived from hematophagous organisms have been reported which are highly potent and specific inhibitors of factor Xa. U.S. Pat. No. 4,588,587 describes anticoagulant activity in the saliva of the Mexican leech, *Haementeria officinalis*. A principal component of this saliva was shown to be the polypeptide factor Xa inhibitor, antistasin (ATS), by Nutt, E. et al., "The Amino Acid Sequence of Antistasin, a Potent Inhibitor of Factor Xa Reveals a Repeated Internal Structure", J. Biol. Chem., 263, 10162–10167 (1988). Another potent and highly specific inhibitor of Factor Xa, called tick anticoagulant peptide (TAP), has been isolated from the whole body extract of the soft tick *Ornithidoros moubata*, as reported by Waxman, L., et al., "Tick Anticoagulant Peptide (TAP) is a Novel Inhibitor of Blood Coagulation Factor Xa" Science, 248, 593–596 (1990).

Factor Xa inhibitory compounds which are not large polypeptide-type inhibitors have also been reported including: Tidwell, R. R. et al., "Strategies for Anticoagulation With Synthetic Protease Inhibitors. Xa Inhibitors Versus Thrombin Inhibitors", Thromb. Res., 19, 339–349 (1980); Turner, A. D. et al., "p-Amidino Esters as Irreversible Inhibitors of Factor IXa and Xa and Thrombin", Biochemistry, 25, 4929–4935 (1986); Hitomi, Y. et al., "Inhibitory Effect of New Synthetic Protease Inhibitor (FUT-175) on the Coagulation System", Haemostasis, 15, 164–168 (1985); Sturzebecher, J. et al., "Synthetic Inhibitors of Bovine Factor Xa and Thrombin. Comparison of Their Anticoagulant Efficiency", Thromb. Res., 54, 245–252 (1989); Kam, C. M. et al., "Mechanism Based Isocoumarin Inhibitors for Trypsin and Blood Coagulation Serine Proteases: New Anticoagulants", Biochemistry, 27 2547–2557 (1988); Hauptmann, J. et al., "Comparison of the Anticoagulant and Antithrombotic Effects of Synthetic Thrombin and Factor Xa Inhibitors", Thromb. Haemost., 63, 220–223 (1990); and the like.

Others have reported Factor Xa inhibitors which are small molecule organic compounds, such as nitrogen containing heterocyclic compounds which have amidino substituent groups, wherein two functional groups of the compounds can bind to Factor Xa at two of its active sites. For example, WO 98/28269 describes pyrazole compounds having a terminal $C(=NH)—NH_2$ group; WO 97/21437 describes benzimidazole compounds substituted by a basic radical which are connected to a naththyl group via a straight or branched chain alkylene,—$C(=O)$ or —$S(=O)_2$ bridging group; WO 99/10316 describes compounds having a 4-phenyl-N-alkylamidino-piperidine and 4-phenoxy-N-alkylamidino-piperidine group connected to a 3-amidinophenyl group via a carboxamidealkyleneamino bridge; and EP 798295 describes compounds having a 4-phenoxy-N-alkylamidino-piperidine group connected to an amidinonaphthyl group via a substituted or unsubstituted sulfonamide or carboxamide bridging group.

There exists a need for effective therapeutic agents for the regulation of hemostasis, and for the prevention and treatment of thrombus formation and other pathological processes in the vasculature induced by thrombin such as restenosis and inflammation. In particular, there continues to be a need for compounds which selectively inhibit factor Xa or its precursors. Compounds that have different combinations of bridging groups and functional groups than compounds previously discovered are needed, particularly compounds which selectively or preferentially bind to Factor Xa. Compounds with a higher degree of binding to Factor Xa than to thrombin are desired, especially those compounds having good bioavailability and/or solubility.

SUMMARY OF THE INVENTION

The present invention relates to novel compounds which inhibit factor Xa, their pharmaceutically acceptable isomers, salts, hydrates, solvates and prodrug derivatives, and pharmaceutically acceptable compositions thereof which have particular biological properties and are useful as potent and specific inhibitors of blood coagulation in mammals. In another aspect, the invention relates to methods of using these inhibitors as diagnostic reagents or as therapeutic agents for disease states in mammals which have coagulation disorders, such as in the treatment or prevention of any thrombotically mediated acute coronary or cerebrovascular syndrome, any thrombotic syndrome occurring in the venous system, any coagulopathy, and any thrombotic complications associated with extracorporeal circulation or instrumentation, and for the inhibition of coagulation in biological samples.

In certain embodiments, this invention relates to novel compounds which are potent and highly selective inhibitors of isolated factor Xa when assembled in the prothrombinase complex. These compounds show selectivity for factor Xa versus other proteases of the coagulation cascade (e.g. thrombin, etc.) or the fibrinolytic cascade, and are useful as diagnostic reagents as well as antithrombotic agents.

In a preferred embodiment, the present invention provides a compound of the formula I:

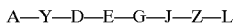

wherein:

A is selected from:
(a) $C_1$–$C_6$-alkyl;
(b) $C_3$–$C_8$-cycloalkyl;
(c) phenyl, which is independently substituted with 0–2 $R^1$ substituents;
(d) naphthyl, which is independently substituted with 0–2 $R^1$ substituents; and
(e) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_1$–$C_4$-alkyl, —CN $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

$R^2$ and $R^3$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0–2;

Y is a member selected from the group consisting of:
a direct link, —C(=O)—, —N($R^4$)—, —C(=O)—N($R^4$)—, —N($R^4$)—C(=O)—, —$SO_2$—, —O—, —$SO_2$—N($R^4$)— and —N($^4$)—$SO_2$—;

$R^4$ is selected from:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

D is a direct link or is a member selected from the group consisting of:
(a) phenyl, which is independently substituted with 0–2 $R^{1a}$ substituents;
(b) naphthyl, which is independently substituted with 0–2 $R^{1a}$ substituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ substituents;

$R^{1a}$ is selected from:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^{2a} R^{3a}$, $SO_2 NR^{2a} R^{3a}$, $SO_2 R^{2a}$, $CF_3$, $OR^{2a}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alynyl, $C_{3-8}$cycloalkyl, $C_{0-4}$alklyl$C_{3-8}$cycloalkyl, —CN and —$NO_2$;

$R^{2a}$ and $R^{3a}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

E is a member selected from the group consisting of:
—N($R^5$)—C(=O)—, —N($R^5$)—C(=O)—$CH_2$—, —C(=O)—N($R^5$)—, —C(=O)—N($R^5$)—$CH_2$—, —N($R^5$)—C(=O)—N($R^6$)—, —$SO_2$—N($R^5$)—, —N($R^5$)—$SO_2$—N($R^6$)— and —N($R^5$)—$SO_2$—N($R^6$)—C(=O)—;

$R^5$ and $R^6$ are independently selected from:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOOC$_{1-4}$alkyl, wherein from 1–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —$NO_2$;

G is selected from:
—$CR^7 R^8$— and —$CR^{7a} R^{8a}$—$CR^{7b} R^{8b}$—
wherein $R^7$, $R^8$, $R^{7a}$, $R^{8a}$, $R^{7b}$ and $R^{8b}$ are independently a member selected from from the group consisting of:

hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylimidazolyl, —$OR^9$, —$C_{0-4}$alkylCOOR$^9$, —$CO_{0-4}$alkylC(=O)NR$^9$R$^{10}$, —$C_{0-4}$alkylC(=O)NR$^9$—CH$_2$—CH$_2$—O—R$^{10}$, —$C_{0-4}$alkylC(=O)NR$^9$(—CH$_2$—CH$_2$—O—R$^{10}$)$_2$, —N(R$^9$)COR$^{10}$, —N(R$^9$)C(=O)R$^{10}$, —N(R$^9$)SO$_2$R$^{10}$, and a naturally occurring or synthetic amino acid side chain, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkyenyl, $C_{3-8}$cycloalkyl, $C_{0-4}$alkyl-$C_{3-8}$cycloalkyl, —CN, —OH, —OC$_{1-4}$alkyl, —OC$_{1-4}$alkyl-OMe, —OCH$_2$COOH, and —NO$_2$;

$R^9$ and $R^{10}$ are independently selected from:
H, $C_{1-4}$alkyl, $C_{03-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$, and wherein $R^9$ and $R^{10}$ taken together can form a 5–8 membered heterocylic ring;

J is a member selected from the group consisting of:
—O—, —O—CH(R$^{11}$)—, —S—, —S(=O)—, —S(=O)$_2$—, —S—CH(R$^{11}$)—, —S(=O)—CH(R$^{11}$)— and —S(=O)$_2$—CH(R$^{11}$)—;

$R^{11}$ is a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylheterocyclic ring having from 1 to 4 hetero ring atoms selected from the group consisting of N, O and S, CH$_2$COOC$_{1-4}$alkyl, CH$_2$COOC$_{1-4}$alkylphenyl and CH$_2$COOC$_{1-4}$alkylnaphthyl;

Z is a member selected from the group consisting of:
(a) phenyl, which is independently substituted with 0–2 R$^{1b}$ substituents;
(a) naphthyl, which is independently substituted with 0–2 R$^{1b}$ substituents; and
(c) a monocyclic or fused bicyclic heterocyclic ring system having from 5 to 10 ring atoms, wherein 1–4 ring atoms of the ring system are selected from N, O and S, and wherein the ring system may be substituted with 0–2 R$^{1b}$ substituents;

$R^{1b}$ is selected from:
Halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, —NO$_2$, NR$^{2b}$R$^{3b}$, SO$_2$NR$^{2b}$R$^{3b}$, SO$_2$R$^{2b}$, CF$_3$, OR$^{2b}$, O—CH$_2$—OPh, O—CH$_2$—Ph, O—CH$_2$—CH$_2$—OR$^{2b}$, O—CH$_2$—COOR$^{2b}$, N(R$^{2b}$)—CH$_2$—CH$_2$—OR$^{2b}$, N(—CH$_2$—CH$_2$—OR$^{2b}$)$_2$, N(R$^{2b}$)—C(=O)R$^{3b}$, N(R$^{2b}$)—SO$_2$—R$^{3b}$, and a 5–6 membered aromatic heterocyclic system containing from 1–4 heteroatoms selected from N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN and —NO$_2$;

$R^{2b}$ and $R^{3b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN and —NO$_2$;

L is selected from:
H, —CN, C(=O)NR$^{12}$R$^{13}$, (CH$_2$)$_n$NR$^{12}$R$^{13}$, C(=NR$^{12}$)NR$^{12}$R$^{13}$, NR$^{12}$R$^{13}$, OR$^{12}$, —NR$^{12}$C(=NR$^{12}$)NR$^{12}$R$^{13}$, and NR$^{12}$C(=NR$^{12}$)—R$^{13}$;

$R^{12}$ and $R^{13}$ are independently selected from:
hydrogen, —OR$^{14}$, —NR$^{14}$R$^{15}$, $C_{1-4}$alkyl, $C_{0-4}$alkylphenyl, $C_{0-4}$alkylnaphthyl, COOC$_{1-4}$alkyl, COO—C$_{0-4}$alkylphenyl and COO—C$_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, and —NO$_2$;

$R^{14}$ and $R^{15}$ are independently selected from:
H, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkylC$_{3-8}$cycloalkyl, —CN, and —NO$_2$;

and all pharmaceutically acceptable isomers, salts, hydrates, solvates and prodrug derivatives thereof.

In certain aspects of this invention, compounds are provided which are useful as diagnostic reagents. In another aspect, the present invention includes pharmaceutical compositions comprising a pharmaceutically effective amount of the compounds of this invention and a pharmaceutically acceptable carrier. In yet another aspect, the present invention includes methods comprising using the above compounds and pharmaceutical compositions for preventing or treating disease states characterized by undesired thrombosis or disorders of the blood coagulation process in mammals, or for preventing coagulation in biological samples such as, for example, stored blood products and samples. Optionally, the methods of this invention comprise administering the pharmaceutical composition in combination with an additional therapeutic agent such as an antithrombotic and/or a thrombolytic agent and/or an anticoagulant.

The preferred compounds also include their pharmaceutically acceptable isomers, hydrates, solvates, salts and prodrug derivatives.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified alkenyl and alkinyl each refer to radicals having from 2–12 carbon atoms.

The term "alkyl" refers to saturated aliphatic groups including straight-chain, branched-chain and cyclic groups having the number of carbon atoms specified, or if no number is specified, having up to 12 carbon atoms. The term "cycloalkyl" as used herein refers to a mono-, bi-, or tricyclic aliphatic ring having 3 to 14 carbon atoms and preferably 3 to 7 carbon atoms.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is aromatic ring ("aryl") having six ring atoms; a stable monocyclic non-aromatic ring having from 3 to 7 ring atoms in the ring; a stable bicyclic ring structure having a total of from 7 to 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from 10 to 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2 bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from loweralkoxy, loweralkyl, loweralkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl, picolyl, naphthylmethyl, phenethyl, benzyhydryl, trityl, and the like, all of which may be optionally substituted.

As used herein, the term "heterocyclic ring" or "heterocyclic ring system" is intended to mean a substituted or unsubstituted member selected from the group consisting of stable monocyclic ring having from 5–7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated non-aromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement (s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocylic and bicyclic heterocylic ring systems, in alphabetical order, are acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl, 1,2,5-thiadiazolyl, 1,3,4- thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl, indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —$CH_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Preferred Embodiments

In a preferred embodiment, the present invention provides a compound according to the formula I:

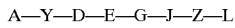

wherein:
A is selected from:
(a) $C_1$–$C_6$-alkyl;
(b) $C_3$–$C_8$-cycloalkyl;
(c) phenyl, which is independently substituted with 0–2 $R^1$ substituents;
(d) naphthyl, which is independently substituted with 0–2 $R^1$ substituents; and
(e) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:
halo, $C_{1-4}$alkyl, —CN, $(CH_2)_m NR^2R^3$, $SO_2NR^2R^3$, $SO_2R^2$, $CF_3$, $OR^2$, and a 5–6 membered aromatic heterocyclic system containing from 1–4 heteroatoms selected from N, O and S;

$R^2$ and $R^3$ are independently selected from the group consisting of:
H, $C_{1-4}$alkyl and $C_{0-4}$alkylaryl, m is an integer of 0–2;

Y is a member selected from the group consisting of:
a direct link, —C(=O)—, —N($R^4$)—, —C(=O)—N($R^4$)—, —N($R^4$)—C(=O)—, —$SO_2$—, —O—, —$SO_2$—N($R^4$)— and —N($R^4$)—$SO_2$—;

$R^4$ is selected from:
H, $C_{1-4}$alkyl and $C_{0-4}$alkylaryl;.

D is absent or is a member selected from the group consisting of:
(a) aryl, which is independently substituted with 0–2 $R^{1a}$ substituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ substituents;

$R^{1a}$ is selected from:
Halo, $C_{1-4}$alkyl, —CN, —$NO_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic ring containing from 1–4 heteroatoms selected from N, O and S;

$R^{2a}$ and $R^{3a}$ are independently selected from the group consisting of:
H, $C_{1-4}$alkyl and $C_{0-4}$alkylaryl;

E is a member selected from the group consisting of:
—N($R^5$)—C(=O)—, —N($R^5$)—C(=O)—CH$_2$—, —C(=O)—N($R^5$)—, —C(=O)—N($R^5$)—CH$_2$—, —N($R^5$)—C(=O)—N($R^6$)—, —SO$_2$—N($R^5$)—, —N($R^5$)—SO$_2$—N($R^6$)— and —N($R^5$)—SO$_2$—N($R^6$)—C(=O)—;

$R^5$ and $R^6$ are independently selected from:
H, $C_{1-4}$alkyl, $C_{0-4}$alkylaryl, $C_{0-4}$alkylheteroaryl, $C_{1-4}$alkylCOOH and $C_{1-4}$alkylCOOC$_{1-4}$alkyl;

G is selected from:
—C$R^7R^8$— and —C$R^{7a}R^{8a}$—C$R^{7b}R^{8b}$—
wherein $R^7$, $R^8$, $R^{7a}$, $R^{8a}$, $R^{7b}$ and $R^{8b}$ are independently a member selected from from the group consisting of:
hydrogen, $C_{1-4}$alkyl, $C_{0-4}$alkyl-$C_{3-8}$cycloalkyl, $C_{0-4}$alkylaryl, —O$R^9$, —$C_{0-4}$alkylCOO$R^9$, —$C_{0-4}$alkylC(=O)N$R^9R^{10}$, —N($R^9$)CO$R^{10}$, —N($R^9$)C(=O)$R^{10}$, —N($R^9$)SO$_2R^{10}$, and common amino acid side chains;

$R^9$ and $R^{10}$ are independently selected from:
H, $C_{1-4}$alkyl and $C_{0-4}$alkylaryl;

J is a member selected from the group consisting of:
—O—, —O—CH($R^{11}$)—, —S— and —S—CH($R^{11}$)—;

$R^{11}$ is a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkylaryl, $C_{0-4}$alkylheterocyclics, CH$_2$COOC$_{1-4}$alkyl, CH$_2$COOC$_{1-4}$alkylaryl;

Z is a member selected from the group consisting of:
(a) aryl, which is independently substituted with 0–2 $R^{1b}$ substituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1b}$ substituents;

$R^{1b}$ is selected from:
halo, $C_{1-4}$alkyl, —CN, —NO$_2$, N$R^{2b}R^{3b}$, SO$_2$N$R^{2b}R^{3b}$, SO$_2R^{2b}$, CF$_3$, O$R^{2b}$, O—CH$_2$—CH$_2$—O$R^{2b}$, O—CH$_2$—COO$R^{2b}$, N($R^{2b}$)—CH$_2$—CH$_2$—O$R^{2b}$, N(—CH$_2$—CH$_2$—O$R^{2b}$)$_2$, N($R^{2b}$)—C(=O)$R^{3b}$, N($R^{2b}$)—SO$_2$—$R^{3b}$, and a 5–6 membered aromatic heterocyclic ring containing from 1–4 heteroatoms selected from N, O and S;

$R^{2b}$ and $R^{3b}$ are independently selected from the group consisting of:
H, $C_{1-4}$alkyl and $C_{0-4}$alkylaryl;

L is selected from:
H, —CN, C(=O)N$R^{12}R^{13}$, (CH$_2$)$_n$N$R^{12}R^{13}$, C(=N$R^{12}$)N$R^{12}R^{13}$, N$R^{12}R^{13}$, O$R^{12}$, —N$R^{12}$C(=N$R^{12}$)N$R^{12}R^{13}$ and N$R^{12}$C(=N$R^{12}$)—$R^{13}$;

$R^{12}$ and $R^{13}$ are independently selected from:
hydrogen, —O$R^{14}$, —N$R^{14}R^{15}$, $C_{1-4}$alkyl, $C_{0-4}$alkylaryl COOC$_{1-4}$alkyl, and COO—$C_{0-4}$ alkylaryl;

$R^{14}$ and $R^{15}$ are independently selected from:
H and $C_{1-4}$alkyl; and and all pharmaceutically acceptable isomers, salts, hydrates, solvates and prodrug derivatives thereof.

In a further preferred embodiment, the present invention provides a compound according to the formula I:

A—Y—D—E—G—J—Z—L wherein:
A is selected from:
(a) phenyl, which is independently substituted with 0–2 $R^1$ substituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^1$ substituents;

$R^1$ is selected from:
halo, (CH$_2$)$_m$N$R^2R^3$, SO$_2$N$R^2R^3$ and SO$_2R^2$;

$R^2$ and $R^3$ are independently selected from the group consisting of:
H and $C_{1-4}$alkyl;

Y is a member selected from the group consisting of:
a direct link, —C(=O)—, —SO$_2$— and —O—;

D is a member selected from the group consisting of:
(a) phenyl, which is independently substituted with 0–2 $R^{1a}$ substituents; and
(b) a monocyclic or fused bicyclic heterocyclic ring system having from 5 to 10 ring atoms, wherein 1–4 ring atoms of the ring system are selected from N, O and S, and wherein the ring system may be substituted with 0–2 $R^{1a}$ substituents;

$R^{1a}$ is selected from:
Halo and $C_{1-4}$alkyl;

$R^{2a}$ and $R^{3a}$ are independently selected from the group consisting of:
H, $C_{1-4}$alkyl, $C_{0-4}$alkylaryl;

E is a member selected from the group consisting of:
—N($R^5$)—C(=O)— and —C(=O)—N($R^5$)—;

$R^5$ and $R^6$ are independently selected from:
H, $C_{1-4}$alkyl, $C_{0-4}$alkylaryl and $C_{0-4}$alkylheteroaryl;

G is selected from:
—C$R^7R^8$— and —C$R^{7a}R^{8a}$—C$R^{7b}R^{8b}$—
wherein $R^7$, $R^8$, $R^{7a}$, $R^{8a}$, $R^{7b}$ and $R^{8b}$ are independently a member selected from from the group consisting of:
hydrogen, $C_{1-4}$alkyl, $C_{0-4}$alkyl-$C_{3-8}$cycloalkyl, $C_{0-4}$alkylaryl, —$C_{0-4}$alkylCOO$R^9$, —O$R^9$, —$C_{0-4}$alkylC(=O) N$R^9R^{10}$, —$C_{0-4}$alkylC(=O)N$R^9$—CH$_2$—CH$_2$—O—$R^{10}$, —$C_{0-4}$alkylC(=O)N$R^9$(—CH$_2$—CH$_2$—O—$R^{10}$)$_2$, —N($R^9$)CO$R^{10}$, —N($R^9$)C(=O)$R^{10}$, —N($R^9$)SO$_2R^{10}$, and common amino acid side chains;

$R^9$ and $R^{10}$ are independently selected from:
H and $C_{1-4}$alkyl, wherein the N$R^9R^{10}$ group of $R^7$, $R^8$, $R^{7a}$, $R^{8a}$, $R^{7b}$ and $R^{8b}$ is optionally cyclized to form a 5–8 membered heterocyclic group;

J is a member selected from the group consisting of:
—O—, —O—CH($R^{11}$)—, —S— and —S—CH($R^{11}$)—;

$R^{11}$ is a member selected from the group consisting of:
hydrogen, $C_{1-4}$alkyl, $C_{2-6}$alkenyl, $C_{0-4}$alkylaryl and a $C_{0-4}$alkylheterocyclic ring;

Z is a member selected from the group consisting of:
(a) phenyl, which is independently substituted with 0–2 $R^{1b}$ substituents;
(b) an aromatic heterocyclic ring having from 5 to 10 ring atoms, wherein 1–4 ring atoms are selected from N, O and S, and wherein the ring may be subsituted independently by from 0–2 $R^{1b}$ substituents; and
(c) a fused aromatic bicyclic heterocyclic ring system having from 5 to 10 ring atoms, wherein 1–4 ring atoms of the ring system are selected from N, O and S, wherein the bicyclic ring system may be substituted with 0–2 $R^{1b}$ substituents;

$R^{1b}$ is selected from:

halo, $C_{1-4}$alkyl, OH, OBn, O—$CH_2$—$CH_2$—OH, O—$CH_2$—$CH_2$—$OCH_3$, O—$CH_2$—COOH, O—$CH_2$—C(=O)—O—$CH_3$, $NH_2$, NH—$CH_2$—$CH_2$—O—$CH_3$, NH—C(=O)—O—$CH_3$, and NH—$SO_2$—$CH_3$;

L is selected from:

H, C(=O)$NR^{12}R^{13}$, $(CH_2)_n NR^{12}R^{13}$ and C(=$NR^{12}$)$NR^{12}R^{13}$;

$R^{12}$ and $R^{13}$ are independently selected from:

hydrogen and $C_{1-4}$alkyl;

and all pharmaceutically acceptable isomers, salts, hydrates, solvates and prodrug derivatives thereof.

In a further preferred embodiment, the present invention provides a compound according to formula I:

A—Y—D—E—G—J—Z—L wherein

A is a member selected from the group consisting of:

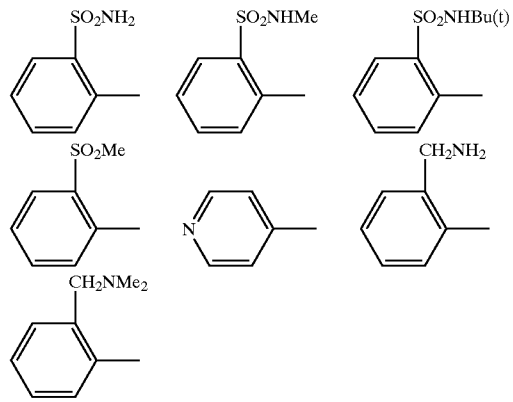

Y is a direct link;

D is a member selected from the group consisting of:

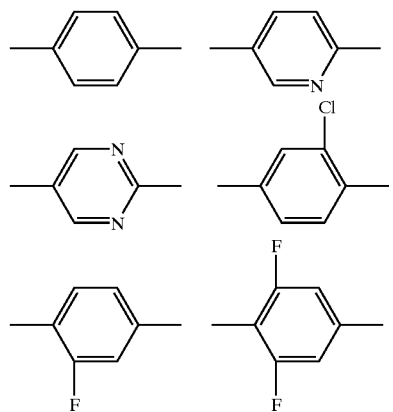

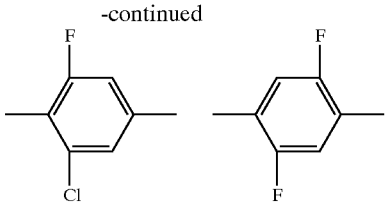

E is a member selected from the group consisting of:
—C(=O)—NH—, —C(=O)—N(—$CH_3$)—, C(=O)—N(—Bn)—, —NH—C(=O)—, —N(—$CH_3$)—C(=O)— and —N(—Bn)C(=O)—;

G is selected from:
—CH—(—$NH_2$)—$CH_2$—, —CH—(—NH(C(=O)—$CH_3$))—$CH_2$—, —CH—(—NH(C(=O)—Ph))—$CH_2$—, —CH—(C(=O)—$OR^8$)—, —CH(—$R^7$)—, —$CH_2$—CH(C(=O)—$OR^8$)—, and —$CH_2$—CH(C(=O)—N(—$R^8$, —$R^8$))—;

$R^7$ is a member selected from the group consisting of:
H, phenyl, Bn, —O-loweralkyl, and cycohexyl;

$R^8$ is a member selected from the group consisting of:
H, $C_{1-6}$alkyl, —O-loweralkyl and $C_{3-6}$cycloalkyl;

J is a member selected from the group consisting of;
—O—, —O—CH($R^{11}$)—, —S— and —S—CH($R^{11}$)—;

$R^{11}$ is a member selected from the group consisting of:
H, methyl, phenyl and benzyl; and Z and L taken together are a member selected from the group consisting of:

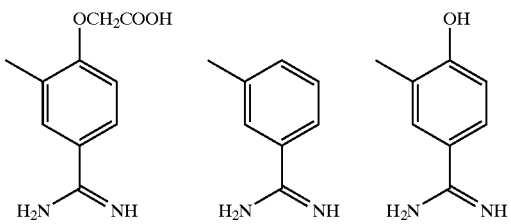

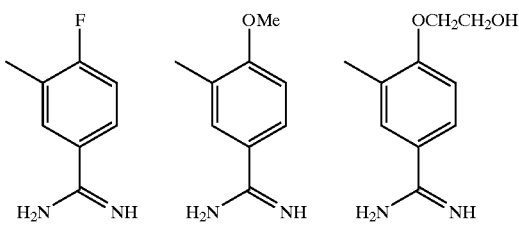

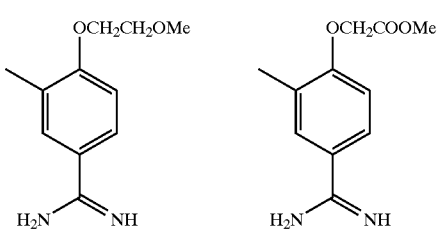

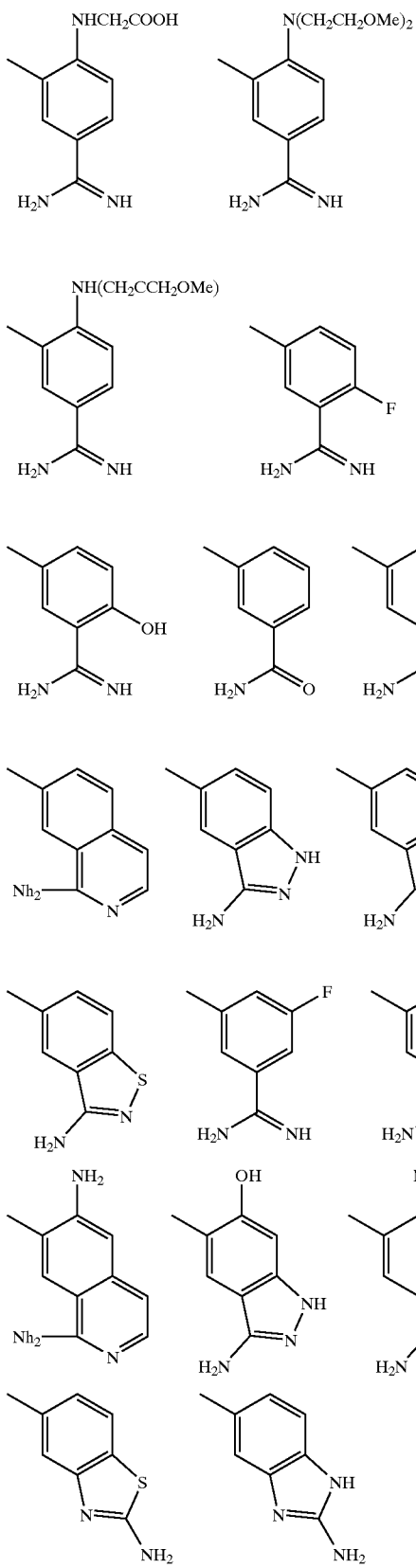

and all pharmaceutically acceptable isomers, salts, hydrates, solvates and prodrug derivatives thereof.

The following non-limiting tables illustrate representative compounds of the present invention:

TABLE 1

Formula II

| $R^7$ | $R^{1b'}$ | $R^{1b''}$ |
|---|---|---|
| H | H | H |
| Me | H | OH |
| (phenyl) | F | H |
| (4-hydroxyphenyl) | —OH | F |
| (cyclohexyl) | Br | OH |
| $CH_2$(phenyl) | —NH2 | OH |
| $CH_2CH_2C(O)O$(cyclopentyl) | OCH2Ph | F |
| $CH_2CH_2C(O)NHMe$ | OCH2CH2OMe | H |
| $CH_2CH_2C(O)NMe_2$ | H | H |
| $CH_2CH_2C(O)$(piperidinyl) | H | H |

TABLE 1a
Formula II
| R⁷ | R¹ᵇ' | R¹ᵇ" |
|---|---|---|
| H | H | H |
| Me | H | OH |
|  | F | H |
|  | —OH | F |
|  | Br | OH |
|  | —NH2 | OH |
|  | OCH2Ph | F |
| 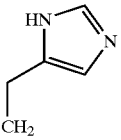 | OCH2CH2OMe | H |
|  | H | H |
TABLE 1a-continued
Formula II
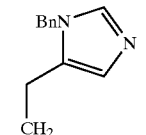
| R⁷ | R¹ᵇ' | R¹ᵇ" |
|---|---|---|
| 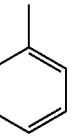 | H | H |
TABLE 2
Formula III
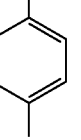
| R⁷ | R¹ᵇ |
|---|---|
| H | H |
| Me | H |
| 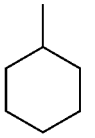 | F |
|  | —OH |
|  | Br |

TABLE 2-continued
Formula III
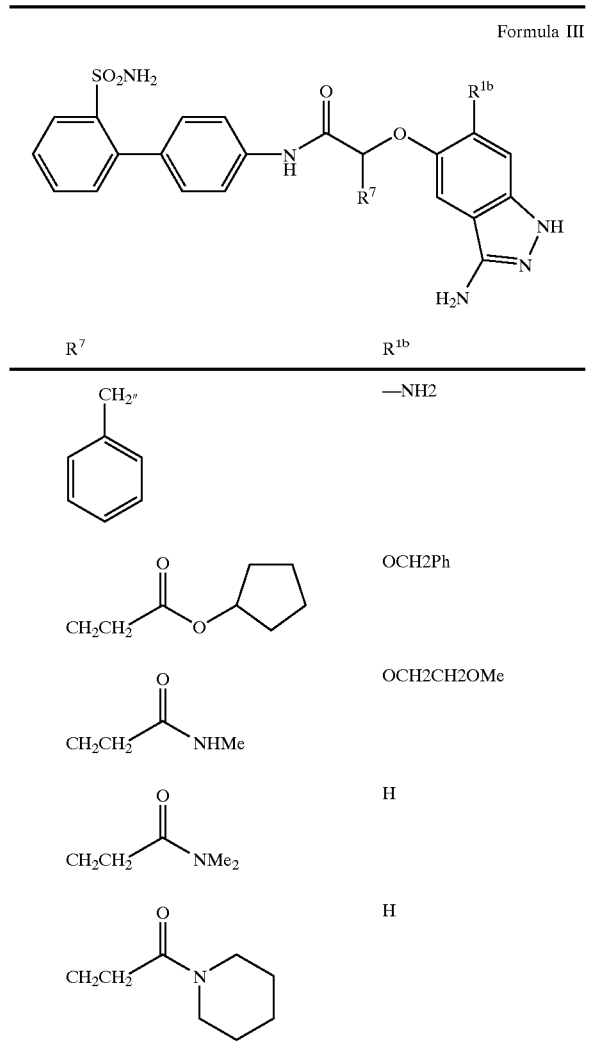
| R⁷ | R¹ᵇ |
|---|---|
| CH₂-Ph (benzyl) | —NH2 |
| CH₂CH₂-C(O)O-cyclopentyl | OCH2Ph |
| CH₂CH₂-C(O)-NHMe | OCH2CH2OMe |
| CH₂CH₂-C(O)-NMe₂ | H |
| CH₂CH₂-C(O)-piperidinyl | H |
TABLE 2a
Formula III
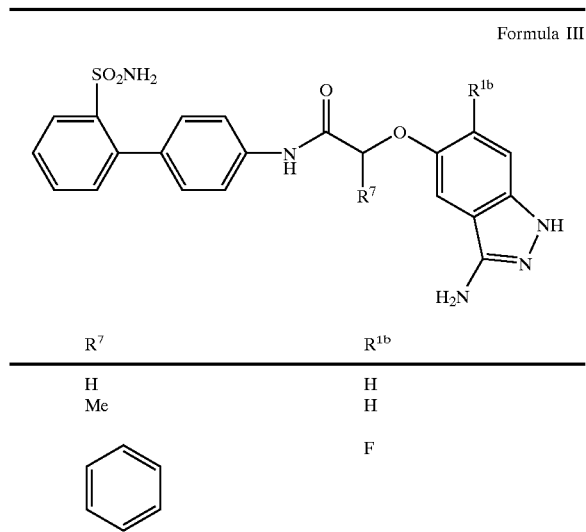
| R⁷ | R¹ᵇ |
|---|---|
| H | H |
| Me | H |
| Ph | F |
TABLE 2a-continued
Formula III
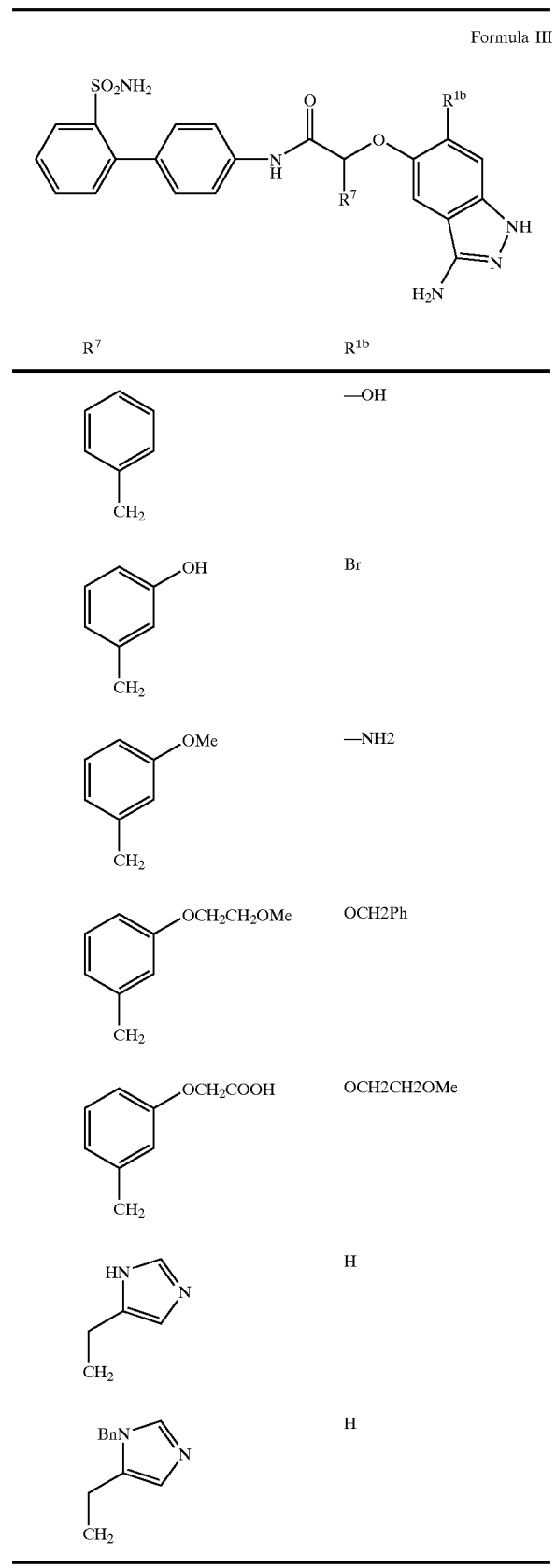
| R⁷ | R¹ᵇ |
|---|---|
| CH₂-Ph | —OH |
| CH₂-(3-hydroxyphenyl) | Br |
| CH₂-(3-methoxyphenyl) | —NH2 |
| CH₂-(3-(OCH2CH2OMe)phenyl) | OCH2Ph |
| CH₂-(3-(OCH2COOH)phenyl) | OCH2CH2OMe |
| CH₂-(1H-imidazol-4-yl) | H |
| CH₂-(1-Bn-imidazol-4-yl) | H |

TABLE 3
Formula IV
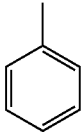
| R⁷ | R¹ᵇ |
|---|---|
| H | H |
| Me | H |
| 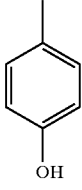 | F |
| 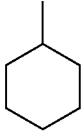 | —OH |
| 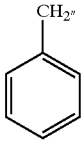 | Br |
| 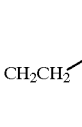 | —NH2 |
|  | OCH2Ph |
| 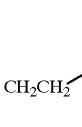 | OCH2CH2OMe |
|  | H |
| 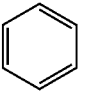 | H |
TABLE 3a
Formula IV
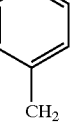
| R⁷ | R¹ᵇ |
|---|---|
| H | H |
| Me | H |
| 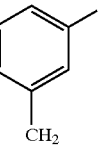 | F |
| 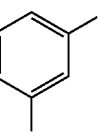 | —OH |
| 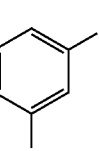 | Br |
| 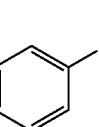 | —NH2 |
| 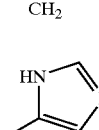 | OCH2Ph |
|  | OCH2CH2OMe |
|  | H |

TABLE 3a-continued

Formula IV

[Structure: 2'-sulfamoylbiphenyl-4-yl amide linked via -NH-C(=O)-CH(R7)-O- to 3-amino-benzo[d]isoxazole with R1b substituent]

| R7 | R1b |
|---|---|
| -CH2-(1-benzyl-imidazol-5-yl) | H |

TABLE 4

Formula V

[Structure: 2'-sulfamoylbiphenyl-4-yl amide linked via -NH-C(=O)-CH(R7)-O- to 3-amino-benzo[d]isothiazole with R1b substituent]

| R7 | R1b |
|---|---|
| H | H |
| Me | H |
| phenyl | F |
| 4-hydroxyphenyl | —OH |
| cyclohexylmethyl | Br |

TABLE 4-continued

Formula V

| R7 | R1b |
|---|---|
| benzyl (CH2Ph) | —NH2 |
| -CH2CH2-C(=O)-O-cyclopentyl | OCH2Ph |
| -CH2CH2-C(=O)-NHMe | OCH2CH2OMe |
| -CH2CH2-C(=O)-NMe2 | H |
| -CH2CH2-C(=O)-N(piperidinyl) | H |

TABLE 4a

Formula V

[Structure: 2'-sulfamoylbiphenyl-4-yl amide linked via -NH-C(=O)-CH(R7)-O- to 3-amino-benzo[d]isothiazole with R1b substituent]

| R7 | R1b |
|---|---|
| H | H |
| Me | H |
| phenyl | F |

TABLE 4a-continued

Formula V

[Structure: 2'-sulfamoyl-biphenyl-4-yl-NH-C(=O)-CH(R7)-O- attached to benzisothiazole with R1b substituent and 3-amino group]

| R7 | R1b |
|---|---|
| benzyl (PhCH2) | —OH |
| 3-hydroxybenzyl (3-HO-C6H4-CH2) | Br |
| 3-methoxybenzyl (3-MeO-C6H4-CH2) | —NH2 |
| 3-(OCH2CH2OMe)benzyl | OCH2Ph |
| 3-(OCH2COOH)benzyl | OCH2CH2OMe |
| (1H-imidazol-5-yl)methyl | H |
| (1-Bn-imidazol-5-yl)methyl | H |

TABLE 5

Formula VI

[Structure: 2'-sulfamoyl-biphenyl-4-yl-NH-C(=O)-CH(R7)-O- attached to 1-aminoisoquinoline with R1b substituent]

| R7 | R1b |
|---|---|
| H | H |
| Me | H |
| 4-methylphenyl (p-tolyl) | F |
| 4-hydroxyphenyl (4-HO-C6H4) | —OH |
| cyclohexyl | Br |
| benzyl (PhCH2) | —NH2 |
| —CH2CH2C(=O)O-cyclopentyl | OCH2Ph |
| —CH2CH2C(=O)NHMe | OCH2CH2OMe |
| —CH2CH2C(=O)NMe2 | H |
| —CH2CH2C(=O)-piperidin-1-yl | H |

TABLE 5a
Formula VI
| R⁷ | R¹ᵇ |
|---|---|
| H | H |
| Me | H |
| 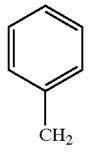 | F |
| 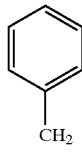 | —OH |
| 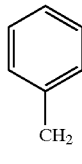 | Br |
| 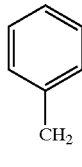 | —NH2 |
| 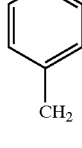 | OCH2Ph |
| 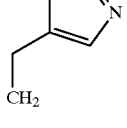 | OCH2CH2OMe |
| 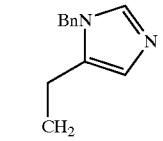 | H |
TABLE 5a-continued
Formula VI
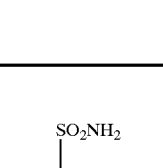
| R⁷ | R¹ᵇ |
|---|---|
| 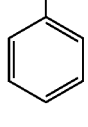 | H |
TABLE 6
Formula VII
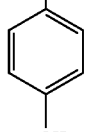
| R⁷ | R¹ᵇ |
|---|---|
| H | H |
| Me | H |
| 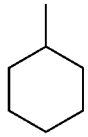 | F |
| 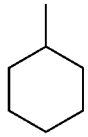 | —OH |
| 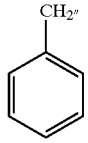 | Br |
| 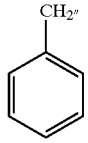 | —NH2 |

TABLE 6-continued

Formula VII

[Structure: 2-sulfamoyl-biphenyl-NH-C(=O)-CH(R⁷)-O-isoquinoline with R¹ᵇ substituent]

| R⁷ | R¹ᵇ |
|---|---|
| CH₂CH₂C(=O)O-cyclopentyl | OCH2Ph |
| CH₂CH₂C(=O)NHMe | OCH2CH2OMe |
| CH₂CH₂C(=O)NMe₂ | H |
| CH₂CH₂C(=O)-piperidine | H |

TABLE 6a

Formula VII

[Structure: 2-sulfamoyl-biphenyl-NH-C(=O)-CH(R⁷)-O-isoquinoline with R¹ᵇ substituent]

| R⁷ | R¹ᵇ |
|---|---|
| H | H |
| Me | H |
| Ph-CH₂ | F |
| Ph-CH₂ | —OH |
| 3-(OH)-C₆H₄-CH₂ | Br |
| 3-(OMe)-C₆H₄-CH₂ | —NH2 |
| 3-(OCH₂CH₂OMe)-C₆H₄-CH₂ | OCH2Ph |
| 3-(OCH₂COOH)-C₆H₄-CH₂ | OCH2CH2OMe |
| (1H-imidazol-4-yl)-CH₂ | H |
| (1-Bn-imidazol-4-yl)-CH₂ | H |

TABLE 7
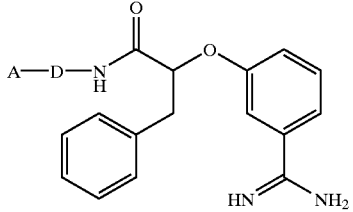

TABLE 8
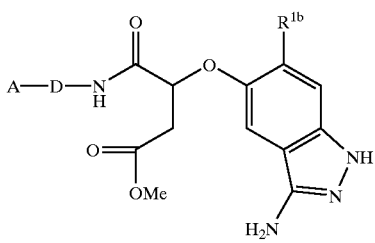
Formula IX
| A | D | A | D |
|---|---|---|---|
| 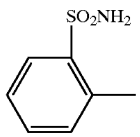 | 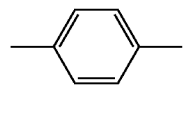 | 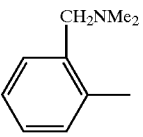 | 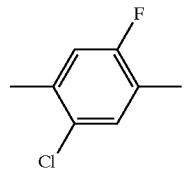 |
| 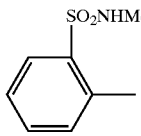 | 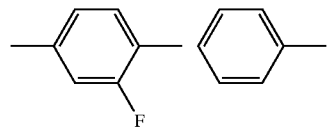 | 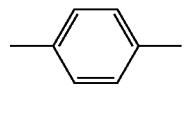 | 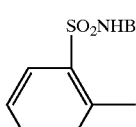 |
| 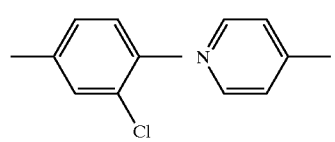 | 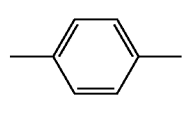 | 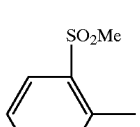 | 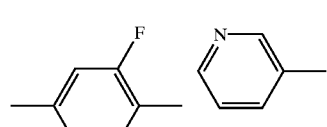 |
| 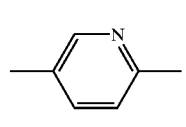 | 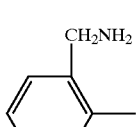 | 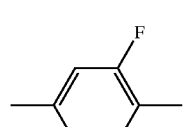 | 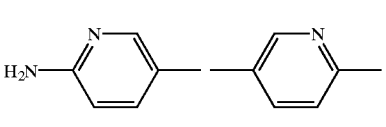 |
| 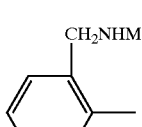 | 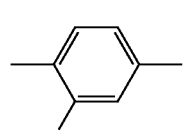 | 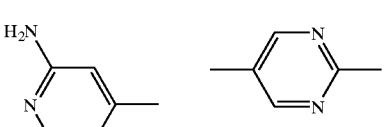 | 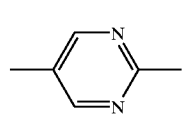 | wherein $R^{1b}$ is a member selected from the group consisting of H, F, —OH, Br, Cl, —NH$_2$, —O—CH$_2$—O—Ph and —O—CH$_2$—CH$_2$—O—CH$_3$,

TABLE 9

Formula X

TABLE 10
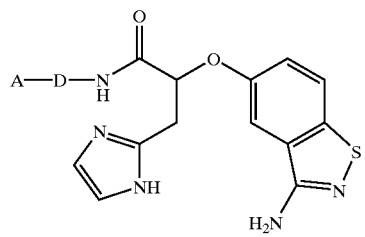
Formula XI
| A | D | A | D |
|---|---|---|---|
| 2-SO₂NH₂-phenyl | 1,4-phenyl | 2-CH₂NMe₂-phenyl | 4-F-2-Cl-phenyl |
| 2-SO₂NHMe-phenyl | 3-F-4-phenyl | phenyl | 1,4-phenyl |
| 2-SO₂NHBu(t)-phenyl | 2-Cl-4-phenyl | 4-pyridyl | 1,4-phenyl |
| 2-SO₂Me-phenyl | 3,4-diF-phenyl | 3-pyridyl | 2,5-pyridyl |
| 2-CH₂NH₂-phenyl | 3,5-diF-phenyl | 6-amino-3-pyridyl | 6-methyl-3-pyridyl |
| 2-CH₂NHMe-phenyl | 3-F-1,4-phenyl | 2-amino-4-pyridyl | 2,5-pyrimidyl |

TABLE 11

Formula XII

Structures of substituents A and D for Formula XII are shown as chemical diagrams.

TABLE 12
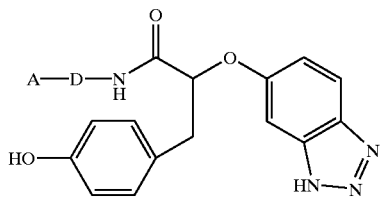
Formula XIII
| A | D | A | D |
|---|---|---|---|
| 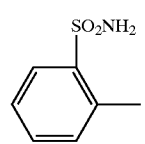 | 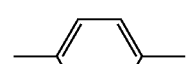 | 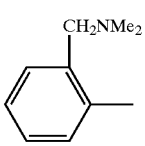 | 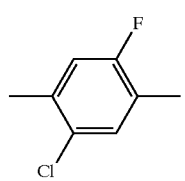 |
| 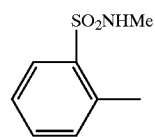 | 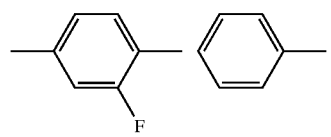 | 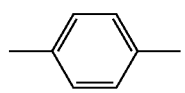 | |
| 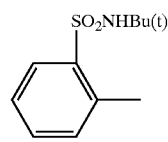 | 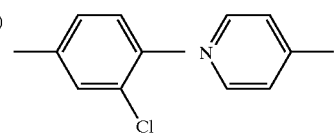 |  | |
| 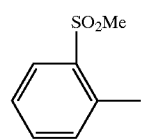 | 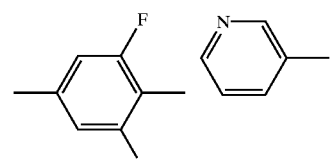 | 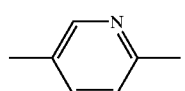 | |
| 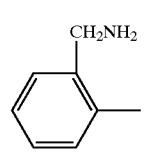 | 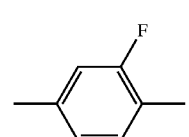 | 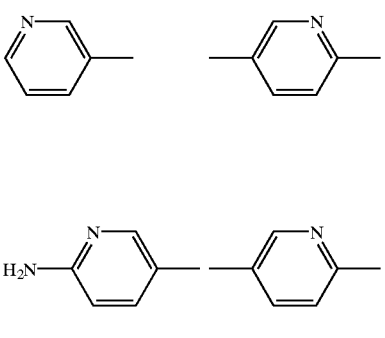 | |
| 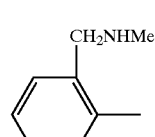 | 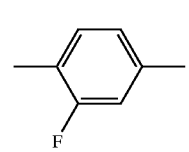 | 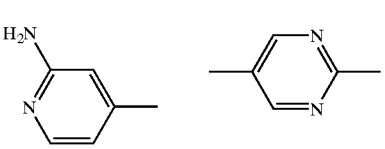 | |

TABLE 13
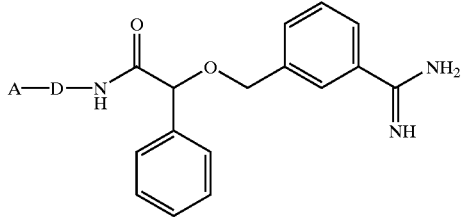
Formula XIV
| A | D | A | D |
|---|---|---|---|
| 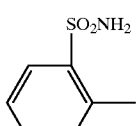 | 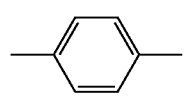 | 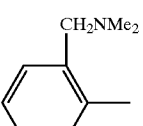 | 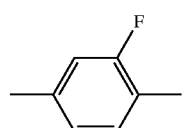 |
| 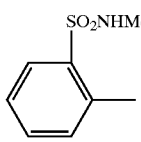 | 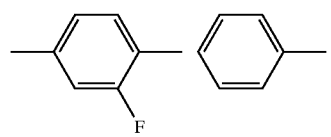 | 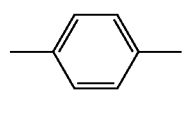 | 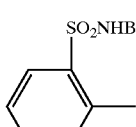 |
| 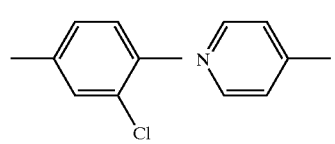 | 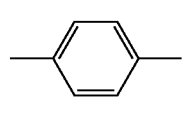 | 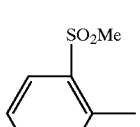 | 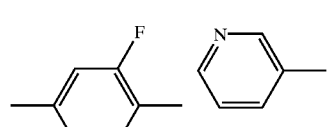 |
| 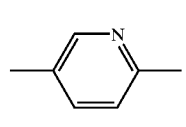 | 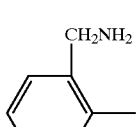 | 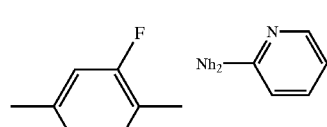 | 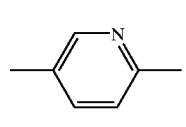 |
| 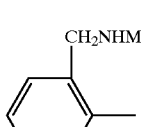 | 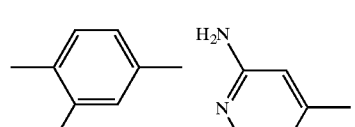 | 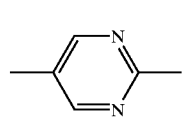 | |

TABLE 14

Formula XV

TABLE 15
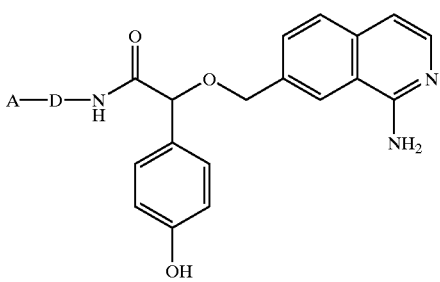

TABLE 16
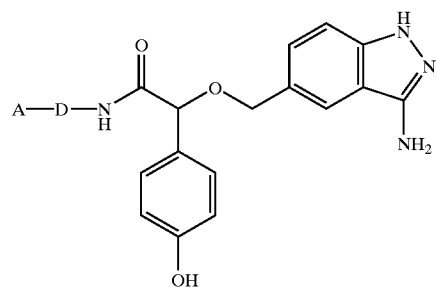
Formula XVII
| A | D | A | D |
|---|---|---|---|
| 2-SO₂NH₂-phenyl | 1,4-phenylene | 2-CH₂NMe₂-phenyl | 2-Cl-5-F-1,4-phenylene |
| 2-SO₂NHMe-phenyl | 2-F-1,4-phenylene | phenyl | 1,4-phenylene |
| 2-SO₂NHBu(t)-phenyl | 2-Cl-1,4-phenylene | 4-pyridyl | 1,4-phenylene |
| 2-SO₂Me-phenyl | 2,3-di-F-1,4-phenylene | 3-pyridyl | 2,5-pyridyl |
| 2-CH₂NH₂-phenyl | 2,5-di-F-1,4-phenylene | 6-NH₂-3-pyridyl | 2,5-pyridyl |
| 2-CH₂NHMe-phenyl | 2-F-1,4-phenylene | 2-NH₂-4-pyridyl | 2,5-pyrimidyl |

TABLE 17

Formula XVIII

| R⁷ | R¹¹ | R¹ᵇ' | R¹ᵇ" |
|---|---|---|---|
| H | H | H | H |
| Me | H | H | OH |
| 4-methylphenyl | phenyl | F | H |
| 4-hydroxyphenyl | benzyl | —OH | F |
| cyclohexyl | 3-hydroxybenzyl | OH | OH |
| benzyl | 3-methoxybenzyl | —NH2 | H |

TABLE 18

Formula XX

| R⁷ | R¹¹ | R⁷ | R¹¹ |
|---|---|---|---|
| H | H | | |
| | | 4-methylphenyl | benzyl |

TABLE 18-continued

Formula XX

| R⁷ | R¹¹ | R⁷ | R¹¹ |
|---|---|---|---|
| Me | H | cyclohexyl | 3-hydroxybenzyl |
| 4-methylphenyl | phenyl | benzyl | 3-methoxybenzyl |

TABLE 19

Formula XX

| R⁷ | R¹¹ | R⁷ | R¹¹ |
|---|---|---|---|
| H | H | | |
| | | 4-hydroxyphenyl | benzyl |
| Me | H | cyclohexyl | 3-hydroxybenzyl |
| 4-methylphenyl | phenyl | benzyl | 3-methoxybenzyl |

TABLE 20
Formula XXII
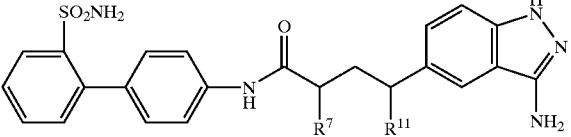
| R⁷ | R¹¹ | R⁷ | R¹¹ |
|---|---|---|---|
| H | H | 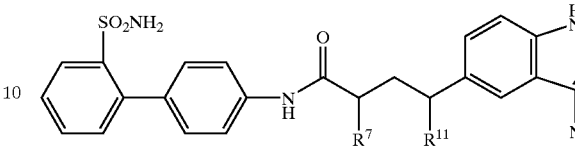 | 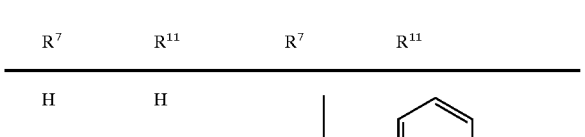 |
| Me | H | 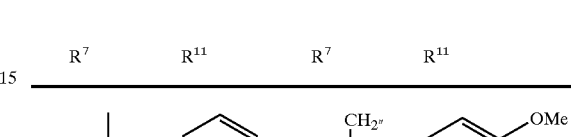 | 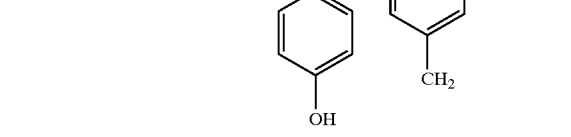 |
| 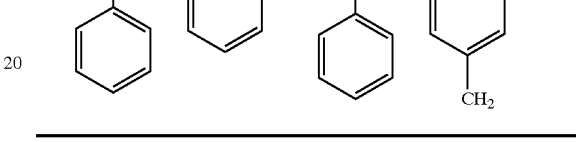 | 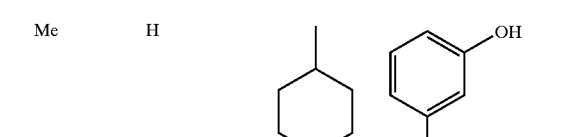 | 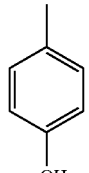 | 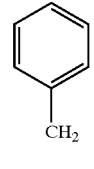 |
TABLE 21
Formula XXII
| R⁷ | R¹¹ | R⁷ | R¹¹ |
|---|---|---|---|
| H | H | 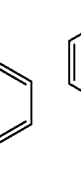 | 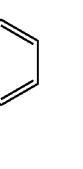 |
| Me | H | 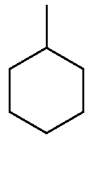 | 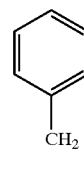 |
TABLE 21-continued
Formula XXII
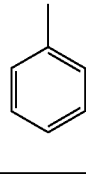
| R⁷ | R¹¹ | R⁷ | R¹¹ |
|---|---|---|---|
| 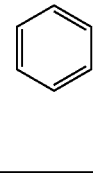 | 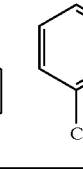 |  | 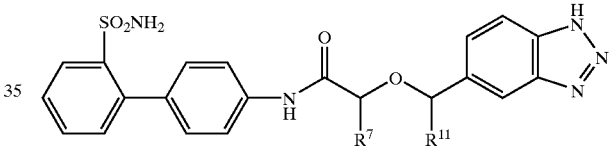 |
TABLE 22
Formula XXIV
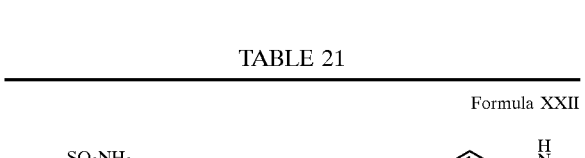
| R⁷ | R¹¹ | R⁷ | R¹¹ |
|---|---|---|---|
| H | H | 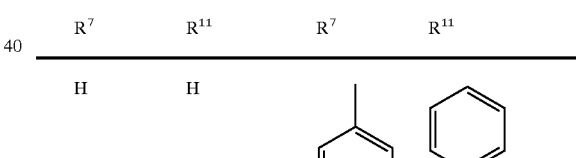 | 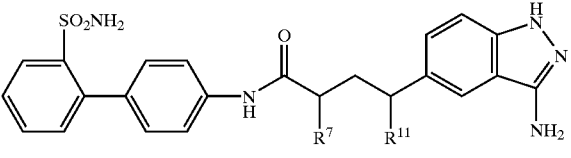 |
| Me | H | 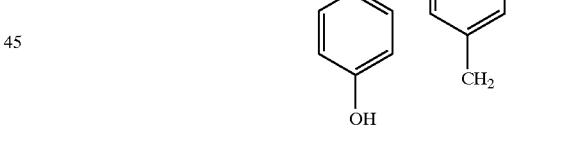 | 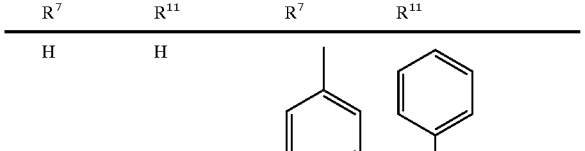 |
| 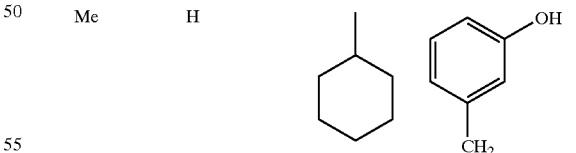 | 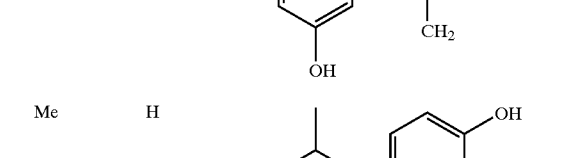 | 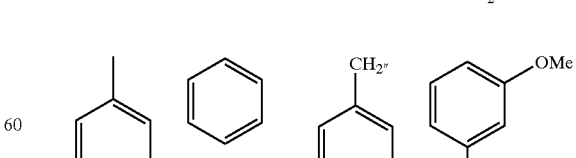 | 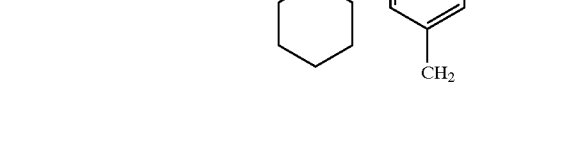 |

TABLE 23

Formula XXIV

| R⁷ | R¹¹ | R⁷ | R¹¹ |
|---|---|---|---|
| H | H | 4-hydroxyphenyl | phenyl-CH₂ |
| Me | H | cyclohexyl | 3-hydroxyphenyl-CH₂ |
| 4-methylphenyl | phenyl | phenyl-CH₂" | 3-methoxyphenyl-CH₂ |

TABLE 24

Formula XXV

| R⁷ | R¹¹ | R⁷ | R¹¹ |
|---|---|---|---|
| H | H | 4-hydroxyphenyl | phenyl-CH₂ |
| Me | H | cyclohexyl | 3-hydroxyphenyl-CH₂ |

TABLE 24-continued

Formula XXV

| R⁷ | R¹¹ | R⁷ | R¹¹ |
|---|---|---|---|
| 4-methylphenyl | phenyl | phenyl-CH₂" | 3-methoxyphenyl-CH₂ |

TABLE 25

Formula XXVI

| R⁷ᵃ | R⁷ᵇ | R¹ᵇ' | R¹ᵇ'' |
|---|---|---|---|
| H | H | H | H |
| Me | H | H | OH |
| 4-methylphenyl | phenyl | F | H |
| 4-hydroxyphenyl | phenyl-CH₂ | —OH | F |
| cyclohexyl | 3-hydroxyphenyl-CH₂ | OH | OH |
| phenyl-CH₂" | 3-methoxyphenyl-CH₂ | —NH2 | H |

TABLE 26

Formula XXVII

| R⁷ᵃ | R⁷ᵇ | R⁷ᵃ | R⁷ᵇ |
|---|---|---|---|
| H | H | 4-methylphenyl (with OH para) | phenyl-CH₂ |
| Me | H | cyclohexyl | 3-hydroxyphenyl-CH₂ |
| | | methylphenyl, phenyl | benzyl (CH₂″), 3-methoxyphenyl-CH₂ |

TABLE 27

Formula XXVIII

| R⁷ᵃ | R⁷ᵇ | R⁷ᵃ | R⁷ᵇ |
|---|---|---|---|
| H | H | 4-hydroxyphenyl | phenyl-CH₂ |
| Me | H | cyclohexyl | 3-hydroxyphenyl-CH₂ |

TABLE 27-continued

Formula XXVIII

| R⁷ᵃ | R⁷ᵇ | R⁷ᵃ | R⁷ᵇ |
|---|---|---|---|
| methylphenyl | phenyl | benzyl (CH₂″) | 3-methoxyphenyl-CH₂ |

TABLE 28

Formula XXX

| R⁷ᵃ | R⁷ᵇ | R⁷ᵃ | R⁷ᵇ |
|---|---|---|---|
| H | H | 4-hydroxyphenyl | phenyl-CH₂ |
| Me | H | cyclohexyl | 3-hydroxyphenyl-CH₂ |
| methylphenyl | phenyl | benzyl (CH₂″) | 3-methoxyphenyl-CH₂ |

TABLE 29

Formula XXX

| R⁷ᵃ | R⁷ᵇ | R⁷ᵃ | R⁷ᵇ |
|---|---|---|---|
| H | H | 4-hydroxyphenyl | benzyl (CH₂-phenyl) |
| Me | H | cyclohexylmethyl | 3-hydroxybenzyl |
| 4-methylphenyl | phenyl | benzyl | 3-methoxybenzyl |

TABLE 30

Formula XXXI

| R⁷ᵃ | R⁷ᵇ | R⁷ᵃ | R⁷ᵇ |
|---|---|---|---|
| H | H | 4-hydroxyphenyl | benzyl |
| Me | H | cyclohexylmethyl | 3-hydroxybenzyl |

TABLE 30-continued

Formula XXXI

| R⁷ᵃ | R⁷ᵇ | R⁷ᵃ | R⁷ᵇ |
|---|---|---|---|
| 4-methylphenyl | phenyl | benzyl | 3-methoxybenzyl |

TABLE 31

Formula XXXII

| R⁷ᵃ | R⁷ᵇ | R⁷ᵃ | R⁷ᵇ |
|---|---|---|---|
| H | H | 4-hydroxyphenyl | benzyl |
| Me | H | cyclohexylmethyl | 3-hydroxybenzyl |
| 4-methylphenyl | phenyl | benzyl | 3-methoxybenzyl |

TABLE 32
Formula XXXIII
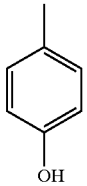
| $R^{7a}$ | $R^{7b}$ | $R^{7a}$ | $R^{7b}$ |
|---|---|---|---|
| H | H | 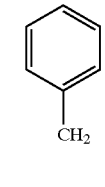 | 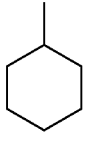 |
| Me | H | 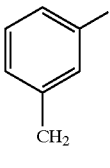 | 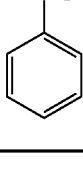 |
| 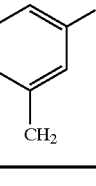 | 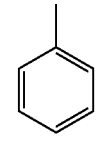 | 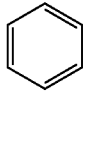 | 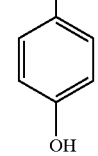 |
TABLE 33
Formula XXXIV
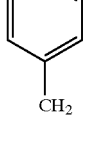
| $R^{7a}$ | $R^{7b}$ | $R^{1b'}$ | $R^{1b''}$ |
|---|---|---|---|
| H | H | H | H |
| Me | H | H | OH |
| 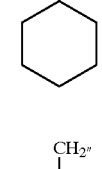 |  | F | H |
| 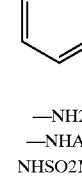 | 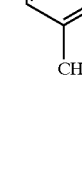 | —OH | F |
| 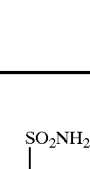 | 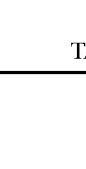 | OH | OH |
|  | 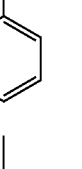 | —NH2 | H |
| —NH2 | Me | H | F |
| —NHAc | Me | H | H |
| NHSO2Me | Me | H | H |
TABLE 34
Formula XXXV
| $R^{7a}$ | $R^{7b}$ |
|---|---|
| H | H |
| Me | H |
| 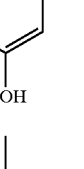 |  |
|  | (cont.) |

TABLE 34-continued
Formula XXXV
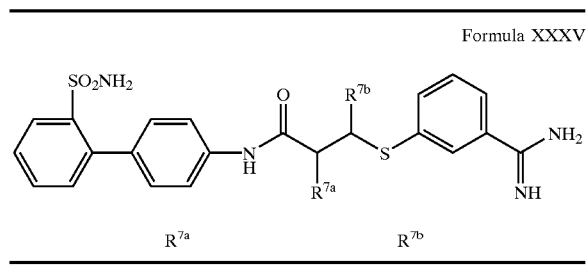
| R⁷ᵃ | R⁷ᵇ |
|---|---|
| 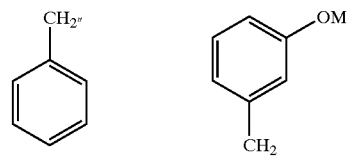 | |
| —NH2 | Me |
| —NHAc | Me |
| NHSO2Me | Me |
TABLE 35
Formula XXXVI
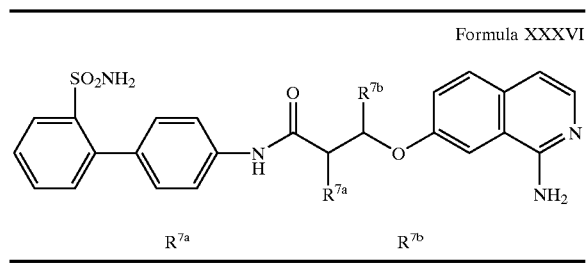
| R⁷ᵃ | R⁷ᵇ |
|---|---|
| H | H |
| Me | H |
| 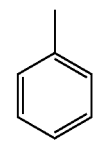 |  |
| 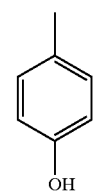 | 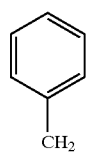 |
| 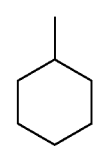 | 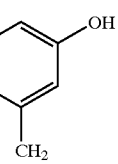 |
| 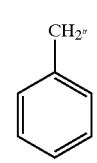 | 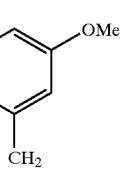 |
| —NH2 | Me |
TABLE 35-continued
Formula XXXVI
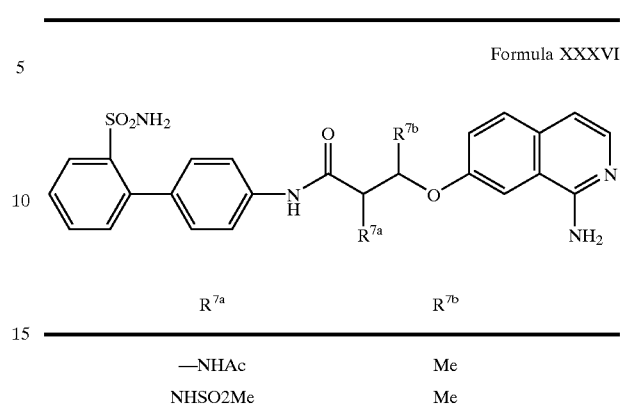
| R⁷ᵃ | R⁷ᵇ |
|---|---|
| —NHAc | Me |
| NHSO2Me | Me |
TABLE 36
Formula XXXVII
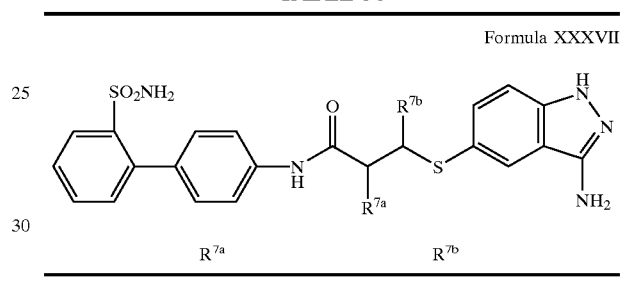
| R⁷ᵃ | R⁷ᵇ |
|---|---|
| H | H |
| Me | H |
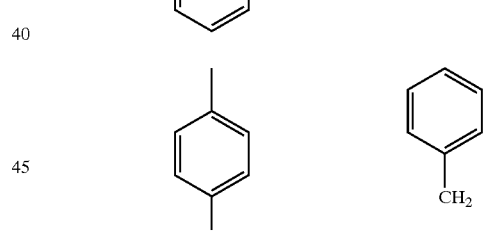
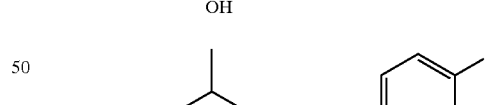
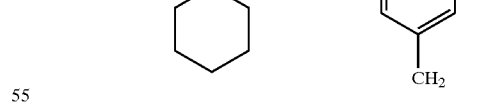
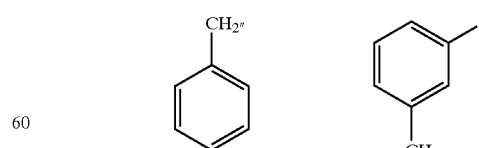
| —NH2 | Me |
| —NHAc | Me |
| NHSO2Me | Me |
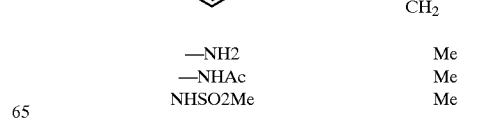

TABLE 37
Formula XXXVIII
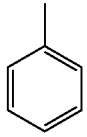
| $R^{7a}$ | $R^{7b}$ |
|---|---|
| H | H |
| Me | H |
| 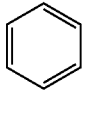 | 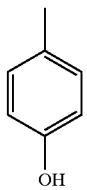 |
| 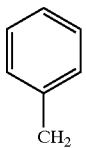 | 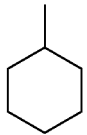 |
| 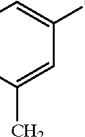 | 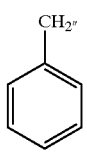 |
| 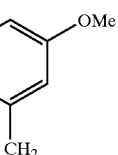 | 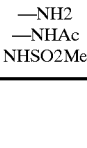 |
| —NH2 | Me |
| —NHAc | Me |
| NHSO2Me | Me |
TABLE 38
Formula XXIX
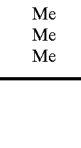
| $R^{7a}$ | $R^{7b}$ |
|---|---|
| H | H |
| Me | H |
| 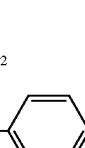 | 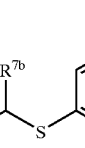 |
TABLE 38-continued
Formula XXIX
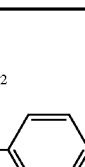
| $R^{7a}$ | $R^{7b}$ |
|---|---|
| 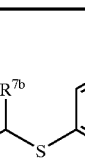 | 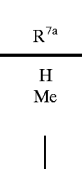 |
| 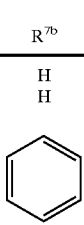 | 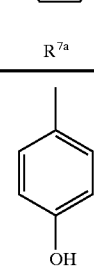 |
| 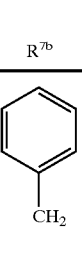 | 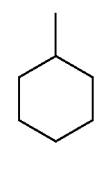 |
| —NH2 | Me |
| —NHAc | Me |
| NHSO2Me | Me |
TABLE 39
Formula XXXX
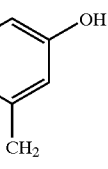
| $R^{7a}$ | $R^{7b}$ |
|---|---|
| H | H |
| Me | H |
| 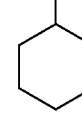 | 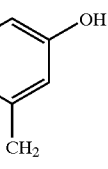 |
| 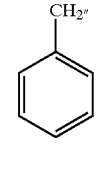 | 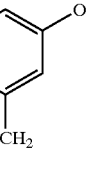 |

TABLE 39-continued

Formula XXXX

| R⁷ᵃ | R⁷ᵇ |
|---|---|
| cyclohexyl | 3-hydroxyphenyl-CH₂ |
| phenyl-CH₂" | 3-methoxyphenyl-CH₂ |
| —NH2 | Me |
| —NHAc | Me |
| NHSO2Me | Me |

TABLE 40

Formula XXXXI

| R⁷ᵃ | R⁷ᵇ |
|---|---|
| H | H |
| Me | H |
| 4-methylphenyl | phenyl |
| 4-hydroxy-4-methylphenyl | phenyl-CH₂ |
| cyclohexyl | 3-hydroxyphenyl-CH₂ |

TABLE 40-continued

Formula XXXXI

| R⁷ᵃ | R⁷ᵇ |
|---|---|
| phenyl-CH₂" | 3-methoxyphenyl-CH₂ |
| —NH2 | Me |
| —NHAc | Me |
| NHSO2Me | Me |

TABLE 41

Formula XXXXII

| R⁷ᵃ | R⁷ᵇ | R¹ᵇ' | R¹ᵇ" |
|---|---|---|---|
| H | H | H | H |
| —C(=O)NCH2CH2OCH3 | H | H | OH |
| 4-methylphenyl | phenyl | F | H |
| 4-hydroxy-4-methylphenyl | phenyl-CH₂ | —OH | F |
| cyclohexyl | 3-hydroxyphenyl-CH₂ | OH | OH |
| phenyl-CH₂" | 3-methoxyphenyl-CH₂ | —NH2 | H |
| —COOH | Me | H | F |
| —COOCH3 | Me | H | H |

TABLE 41-continued
Formula XXXXII
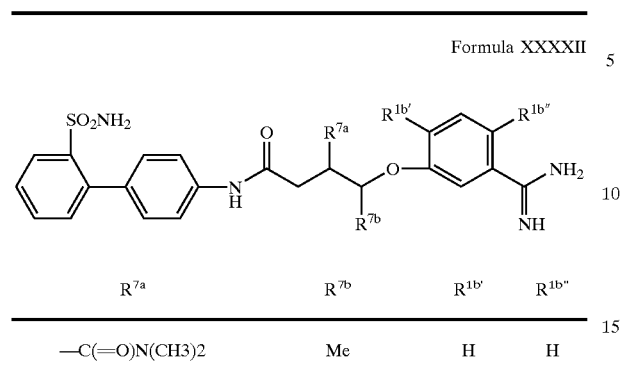
| R<sup>7a</sup> | R<sup>7b</sup> | R<sup>1b'</sup> | R<sup>1b"</sup> |
|---|---|---|---|
| —C(=O)N(CH3)2 | Me | H | H |
TABLE 42
Formula XXXXIII
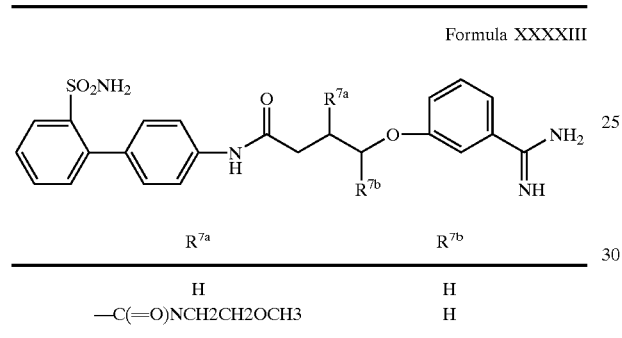
| R<sup>7a</sup> | R<sup>7b</sup> |
|---|---|
| H | H |
| —C(=O)NCH2CH2OCH3 | H |
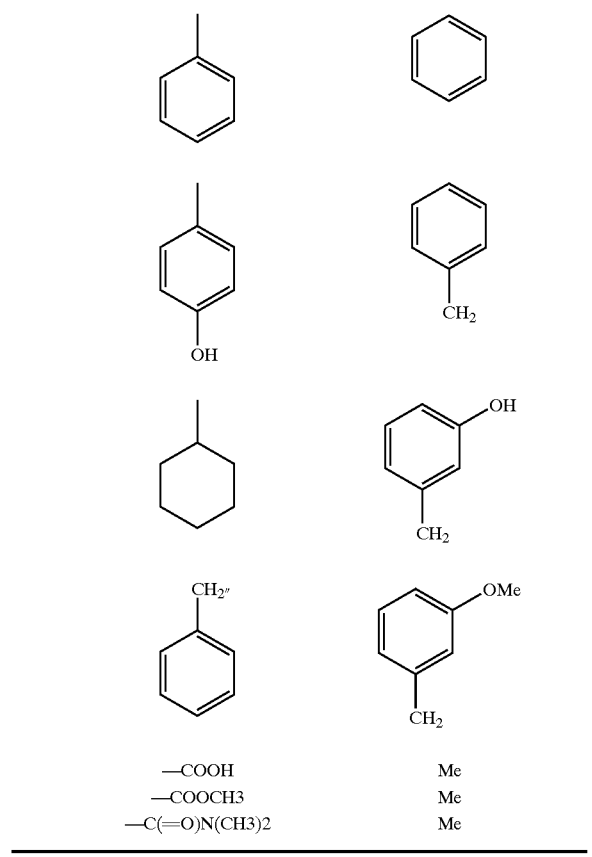
| —COOH | Me |
| —COOCH3 | Me |
| —C(=O)N(CH3)2 | Me |
TABLE 43
Formula XXXXIV
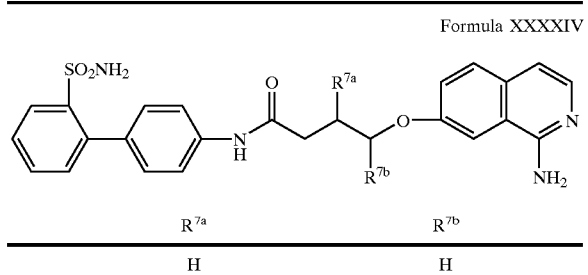
| R<sup>7a</sup> | R<sup>7b</sup> |
|---|---|
| H | H |
| —C(=O)NCH2CH2OCH3 | H |
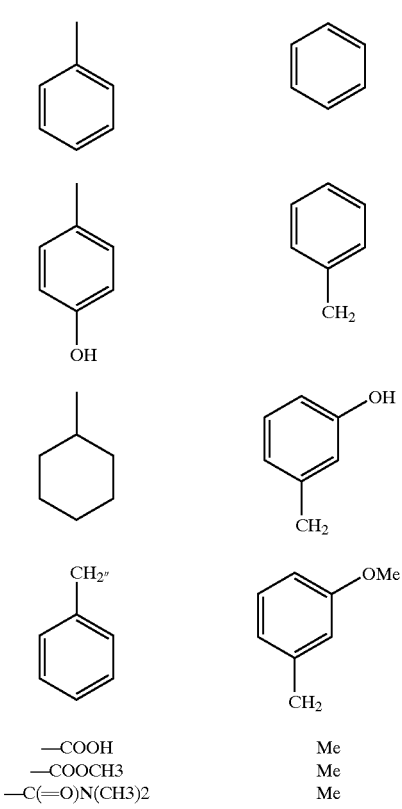
| —COOH | Me |
| —COOCH3 | Me |
| —C(=O)N(CH3)2 | Me |
TABLE 44
Formula XXXXV
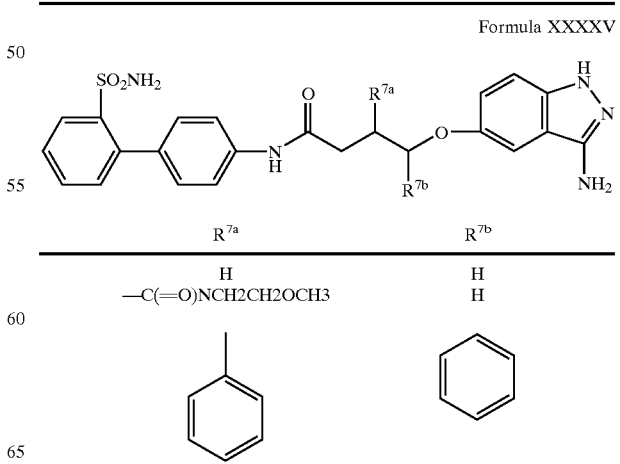
| R<sup>7a</sup> | R<sup>7b</sup> |
|---|---|
| H | H |
| —C(=O)NCH2CH2OCH3 | H |

TABLE 44-continued

Formula XXXXV

| R⁷ᵃ | R⁷ᵇ |
|---|---|
| 4-hydroxyphenyl | benzyl (CH₂-phenyl) |
| cyclohexyl | 3-hydroxybenzyl (CH₂-phenyl-OH) |
| benzyl (CH₂''-phenyl) | 3-methoxybenzyl (CH₂-phenyl-OMe) |
| —COOH | Me |
| —COOCH3 | Me |
| —C(=O)N(CH3)2 | Me |

TABLE 45

Formula XXXXVI

| R⁷ᵃ | R⁷ᵇ |
|---|---|
| H | H |
| —C(=O)NCH2CH2OCH3 | H |
| 4-methylphenyl | phenyl |
| 4-hydroxyphenyl | benzyl (CH₂-phenyl) |

TABLE 45-continued

Formula XXXXVI

| R⁷ᵃ | R⁷ᵇ |
|---|---|
| cyclohexyl | 3-hydroxybenzyl |
| benzyl (CH₂''-phenyl) | 3-methoxybenzyl |
| —COOH | Me |
| —COOCH3 | Me |
| —C(=O)N(CH3)2 | Me |

TABLE 46

Formula XXXXVII

| R⁷ᵃ | R⁷ᵇ |
|---|---|
| H | H |
| —C(=O)NCH2CH2OCH3 | H |
| 4-methylphenyl | phenyl |
| 4-hydroxyphenyl | benzyl |
| cyclohexyl | 3-hydroxybenzyl |

TABLE 46-continued

Formula XXXXVII

[Structure: 2-sulfamoyl-biphenyl-NH-C(=O)-CH2-CHR7a-CHR7b-O-benzisoxazol-3-amine]

| R7a | R7b |
|---|---|
| CH2″–phenyl | 3-methoxybenzyl (CH2-C6H4-OMe) |
| —COOH | Me |
| —COOCH3 | Me |
| —C(=O)N(CH3)2 | Me |

TABLE 47

Formula XXXXVIII

[Structure: 2-sulfamoyl-biphenyl-NH-C(=O)-CH2-CHR7a-CHR7b-O-1H-benzotriazol-5-yl]

| R7a | R7b |
|---|---|
| H | H |
| —C(=O)NCH2CH2OCH3 | H |
| 4-methylphenyl | phenyl |
| 4-hydroxyphenyl | benzyl (CH2-phenyl) |
| cyclohexyl | 3-hydroxybenzyl |

TABLE 47-continued

Formula XXXXVIII

[Structure: 2-sulfamoyl-biphenyl-NH-C(=O)-CH2-CHR7a-CHR7b-O-1H-benzotriazol-5-yl]

| R7a | R7b |
|---|---|
| CH2″–phenyl | 3-methoxybenzyl |
| —COOH | Me |
| —COOCH3 | Me |
| —C(=O)N(CH3)2 | Me |

TABLE 48

Formula XXXXIX

[Structure: 2-sulfamoyl-biphenyl-NH-C(=O)-CH2-CHR7a-CHR7b-O-1H-benzimidazol-2-amine]

| R7a | R7b |
|---|---|
| H | H |
| —C(=O)NCH2CH2OCH3 | H |
| 4-methylphenyl | phenyl |
| 4-hydroxyphenyl | benzyl |
| cyclohexyl | 3-hydroxybenzyl |
| CH2″–phenyl | 3-methoxybenzyl |
| —COOH | Me |

TABLE 48-continued

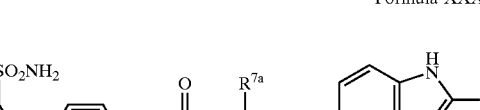

Formula XXXXIX

| $R^{7a}$ | $R^{7b}$ |
|---|---|
| —COOCH3 | Me |
| —C(=O)N(CH3)2 | Me |

TABLE 49

Formula L

| $R^5$ | $R^{7a}$ | $R^{7b}$ | $R^{1b}$ |
|---|---|---|---|
| H | H | H | H |
| Me | Me | H | H |
| phenyl | phenyl | Me | F |
| 4-pyridylmethyl (H2C-pyridine) | benzyl (phenyl-CH2) | Bn | OH |
| cyclohexyl | 3-hydroxybenzyl (OH-phenyl-CH2) | 4-pyridylmethyl (H2C-pyridine) | OMe |
| benzyl (CH2"-phenyl) | 3-methoxybenzyl (OMe-phenyl-CH2) | 3-pyridylmethyl (H2C-pyridine) | OBn |
| H | —CH2OOH | 4-hydroxybenzyl (H2C-phenyl-OH) | OCH2COOH |
| Me | —CH2CH2COOMe | 4-aminobenzyl (H2C-phenyl-NH2) | OCH2CH2OMe |

TABLE 49-continued
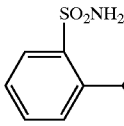
Formula L
| R⁵ | R⁷ᵃ | R⁷ᵇ | R¹ᵇ |
|---|---|---|---|
| Bn | —CH2CH2CONMe2 | 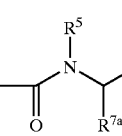 | OH |
TABLE 50
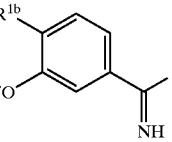
Formula LI
| R⁵ | R⁷ᵃ | R⁷ᵇ |
|---|---|---|
| H | H | H |
| Me | Me | H |
|  | 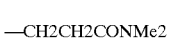 | Me |
| 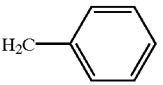 | 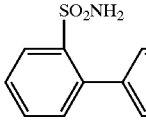 | Bn |
| 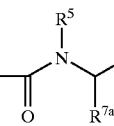 | 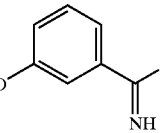 | 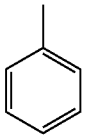 |
| 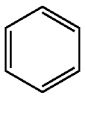 | 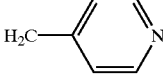 |  |
| H | —CH2OOH | 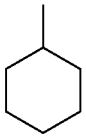 |
| Me | —CH2CH2COOMe | 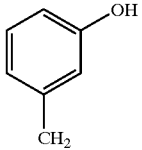 |

TABLE 50-continued
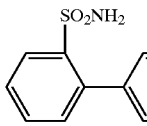
Formula LI
| R⁵ | R⁷ᵃ | R⁷ᵇ |
|---|---|---|
| Bn | —CH2CH2CONMe2 | 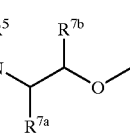 |
TABLE 51
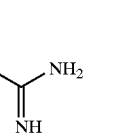
Formula LII
| R⁵ | R⁷ᵃ | R⁷ᵇ |
|---|---|---|
| H | H | H |
| Me | Me | H |
|  |  | Me |
| 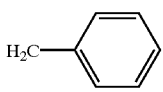 | 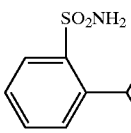 |  |
| 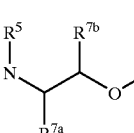 | 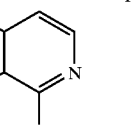 | Bn |
| 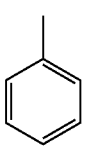 | 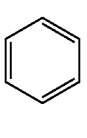 | 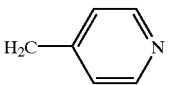 |
| 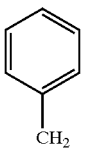 | 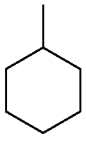 | 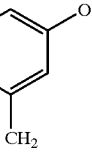 |
| H | —CH2OOH |  |
| Me | —CH2CH2COOMe | 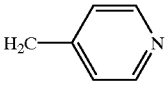 |
|  |  | 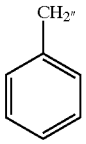 |

TABLE 51-continued

Formula LII

[Structure: 2'-sulfamoyl-biphenyl-4-carboxamide with N(R5)-CH(R7a)-CH(R7b)-O-(1-aminoisoquinolin-7-yl)]

| R⁵ | R⁷ᵃ | R⁷ᵇ |
|---|---|---|
| Bn | —CH2CH2CONMe2 | H2C—Ph (benzyl) |

TABLE 52

Formula LIII

[Structure: 2'-sulfamoyl-biphenyl-4-carboxamide with N(R5)-CH(R7a)-CH(R7b)-O-(3-amino-1H-indazol-5-yl)]

| R⁵ | R⁷ᵃ | R⁷ᵇ |
|---|---|---|
| H | H | H |
| Me | Me | H |
| H2C–(4-methylphenyl) | H2C–Ph | Me |
| H2C–(4-pyridyl) | H2C–Ph | Bn |
| methylcyclohexyl | H2C–(3-hydroxyphenyl) | H2C–(4-pyridyl) |
| CH2″–Ph (benzyl) | H2C–(3-methoxyphenyl) | H2C–(3-pyridyl) |
| H | —CH2OOH | H2C–(4-hydroxyphenyl) |
| Me | —CH2CH2COOMe | H2C–(4-aminophenyl) |

TABLE 52-continued

Formula LIII

[Structure: 2'-sulfamoylbiphenyl-4-carboxamide with N-R5, CHR7a-CHR7b-O-linker to 3-amino-1H-indazol-5-yl]

| R[5] | R[7a] | R[7b] |
|---|---|---|
| Bn | —CH2CH2CONMe2 | benzyl (H2C–Ph) |

TABLE 53

Formula LIV

[Structure: 2'-sulfamoylbiphenyl-4-carboxamide with N-R5, CHR7a-CHR7b-O-linker to 3-amino-1,2-benzisothiazol-5-yl]

| R[5] | R[7a] | R[7b] |
|---|---|---|
| H | H | H |
| Me | Me | H |
| 4-methylphenyl (p-tolyl-CH2?) | phenyl | Me |
| 4-pyridylmethyl (H2C-4-Py) | benzyl (Ph-CH2) | Bn |
| cyclohexylmethyl | 3-hydroxybenzyl (3-HO-C6H4-CH2) | 4-pyridylmethyl (H2C-4-Py) |
| benzyl (CH2-Ph) | 3-methoxybenzyl (3-MeO-C6H4-CH2) | 3-pyridylmethyl (H2C-3-Py) |
| H | —CH2OOH | 4-hydroxybenzyl (H2C-C6H4-OH) |
| Me | —CH2CH2COOMe | 4-aminobenzyl (H2C-C6H4-NH2) |

TABLE 53-continued
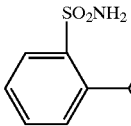
Formula LIV
| R⁵ | R⁷ᵃ | R⁷ᵇ |
|---|---|---|
| Bn | —CH2CH2CONMe2 | 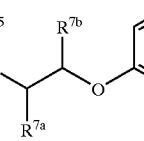 |
TABLE 54
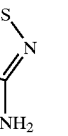
Formula LV
| R⁵ | R⁷ᵃ | R⁷ᵇ |
|---|---|---|
| H | H | H |
| Me | Me | H |
| 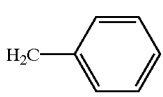 | 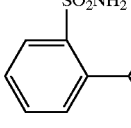 | Me |
| 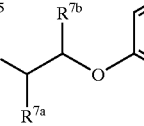 |  | Bn |
| 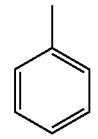 | 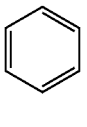 | 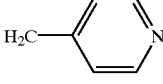 |
|  | 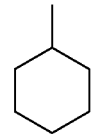 | 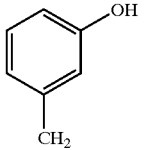 |
| H | —CH2OOH | 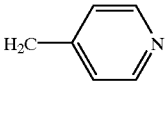 |
| Me | —CH2CH2COOMe | 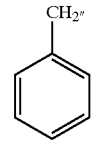 |

TABLE 54-continued
Formula LV
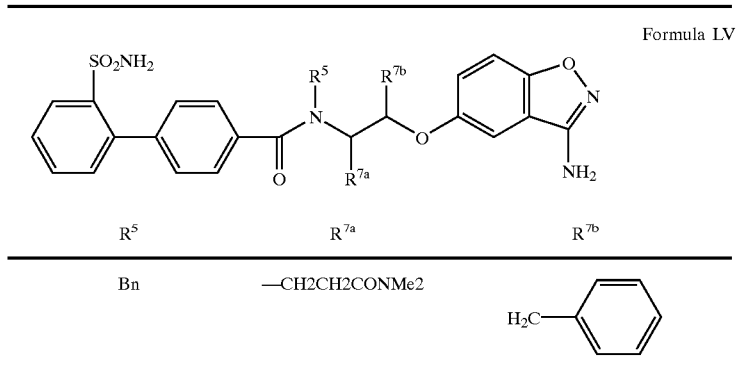
| $R^5$ | $R^{7a}$ | $R^{7b}$ |
|---|---|---|
| Bn | —CH2CH2CONMe2 | H₂C-phenyl |
TABLE 55
Formula LVI
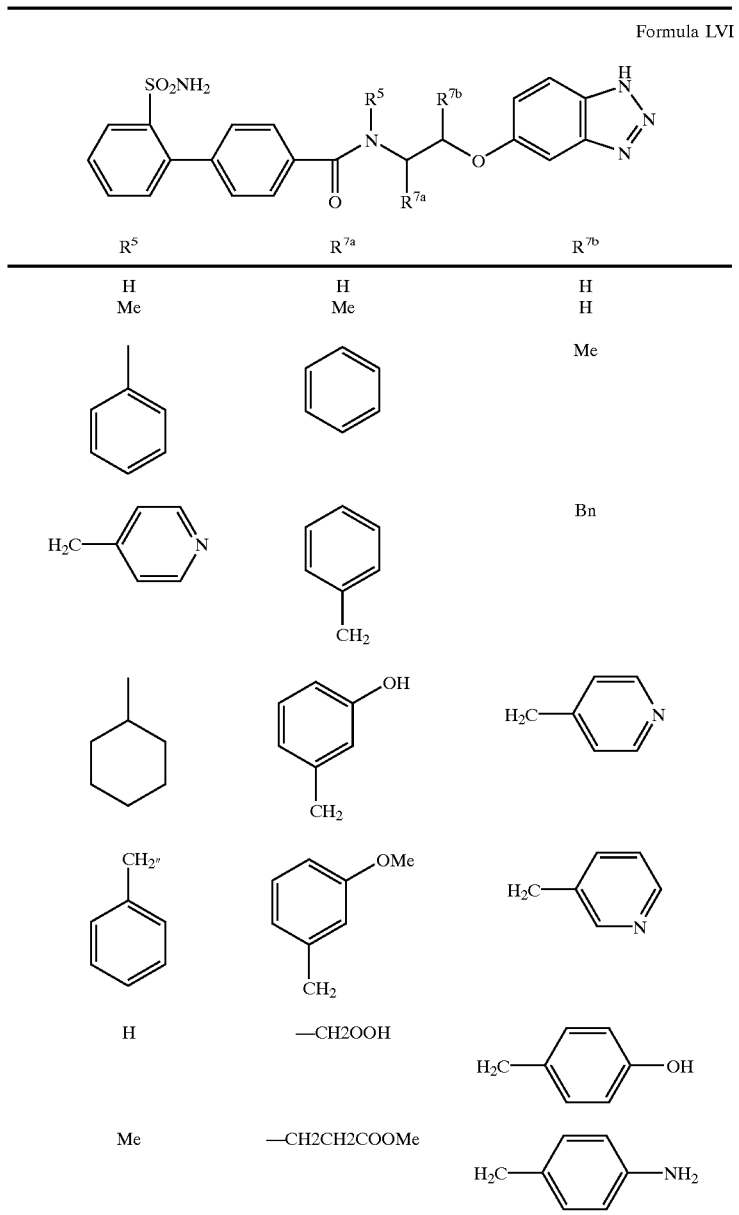
| $R^5$ | $R^{7a}$ | $R^{7b}$ |
|---|---|---|
| H | H | H |
| Me | Me | H |
| | | Me |
| tolyl-CH₂ | phenyl | |
| | | Bn |
| H₂C-(4-pyridyl) | phenyl-CH₂ | |
| | | H₂C-(4-pyridyl) |
| cyclohexyl-CH | 3-hydroxybenzyl-CH₂ | |
| | | H₂C-(3-pyridyl) |
| CH₂″-phenyl | 3-methoxybenzyl-CH₂ | |
| H | —CH2OOH | H₂C-(4-hydroxyphenyl) |
| Me | —CH2CH2COOMe | H₂C-(4-aminophenyl) |

TABLE 55-continued
Formula LVI
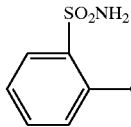
| R⁵ | R⁷ᵃ | R⁷ᵇ |
|---|---|---|
| Bn | —CH2CH2CONMe2 | 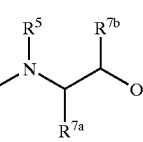 |
TABLE 56
Formula LVII
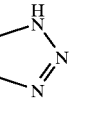
| R⁵ | R⁷ᵃ | R⁷ᵇ |
|---|---|---|
| H | H | H |
| Me | Me | H |
|  | 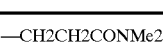 | Me |
| 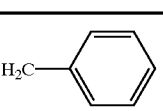 | 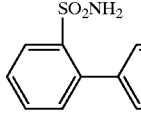 | Bn |
| 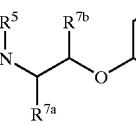 | 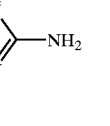 |  |
|  |  |  |
| H | —CH2OOH |  |
| Me | —CH2CH2COOMe |  |

TABLE 56-continued
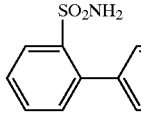
Formula LVII
| R⁵ | R⁷ᵃ | R⁷ᵇ |
|---|---|---|
| Bn | —CH2CH2CONMe2 | 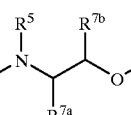 |
TABLE 57
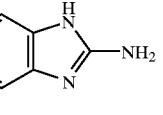
Formula LVIII
| R⁵ | R⁷ᵃ | R⁷ᵇ | R¹ᵇ |
|---|---|---|---|
| H | H | H | H |
| Me | Me | H | H |
|  | 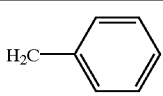 | Me | F |
| 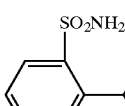 | 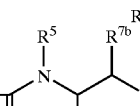 | Bn | OH |
| 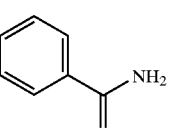 |  | 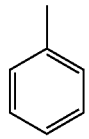 | OMe |
| 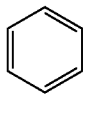 | 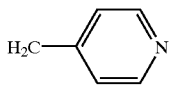 |  | OBn |
| H | —CH2OOH | 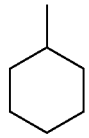 | OCH2COOH |
| Me | —CH2CH2COOMe | 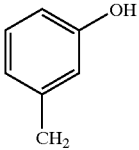 | OCH2CH2OMe |

TABLE 57-continued
Formula LVIII
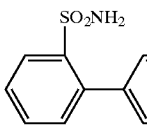
| R⁵ | R⁷ᵃ | R⁷ᵇ | R¹ᵇ |
|---|---|---|---|
| Bn | —CH2CH2CONMe2 | 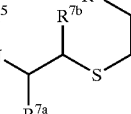 | OH |
TABLE 58
Formula LIX
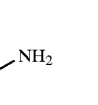
| R⁵ | R⁷ᵃ | R⁷ᵇ |
|---|---|---|
| H | H | H |
| Me | Me | H |
| | | Me |
|  | 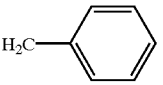 | |
| 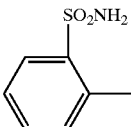 | 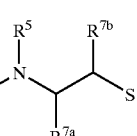 | Bn |
| 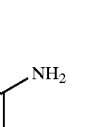 | 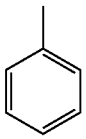 | 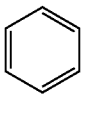 |
| 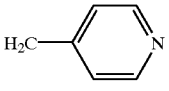 |  | 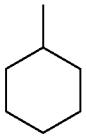 |
| H | —CH2OOH | 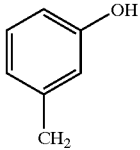 |
| Me | —CH2CH2COOMe | 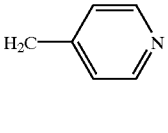 |

TABLE 58-continued

Formula LIX

[Structure: 2-sulfamoyl-biphenyl-4-carboxamide with N(R⁵), CH(R⁷ᵃ)-CH(R⁷ᵇ)-S-(3-amidinophenyl)]

| R⁵ | R⁷ᵃ | R⁷ᵇ |
|---|---|---|
| Bn | —CH2CH2CONMe2 | H₂C—C₆H₅ (benzyl) |

TABLE 59

Formula LX

[Structure: 2-sulfamoyl-biphenyl-4-carboxamide with N(R⁵), CH(R⁷ᵃ)-CH(R⁷ᵇ)-S-(1-aminoisoquinolin-7-yl)]

| R⁵ | R⁷ᵃ | R⁷ᵇ |
|---|---|---|
| H | H | H |
| Me | Me | H |
|  |  | Me |
| phenyl | phenyl |  |
|  |  | Bn |
| H₂C-(4-pyridyl) | benzyl (CH₂-C₆H₅) |  |
|  |  | H₂C-(4-pyridyl) |
| cyclohexylmethyl | 3-hydroxybenzyl |  |
| CH₂-phenyl (benzyl) | 3-methoxybenzyl | H₂C-(3-pyridyl) |
| H | —CH2OOH |  |
|  |  | H₂C-(4-hydroxyphenyl) |
| Me | —CH2CH2COOMe |  |
|  |  | H₂C-(4-aminophenyl) |

TABLE 59-continued
Formula LX
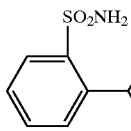
| R[5] | R[7a] | R[7b] |
|---|---|---|
| Bn | —CH2CH2CONMe2 | 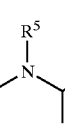 |
TABLE 60
Formula LXI
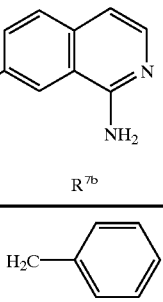
| R[5] | R[7a] | R[7b] |
|---|---|---|
| H | H | H |
| Me | Me | H |
| 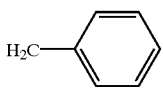 | 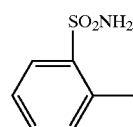 | Me |
| 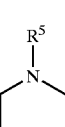 | 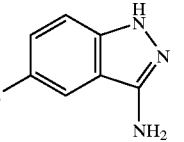 | Bn |
| 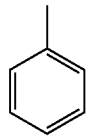 | 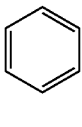 | 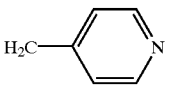 |
|  | 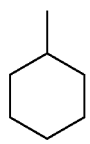 | 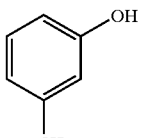 |
| H | —CH2OOH | 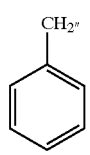 |
| Me | —CH2CH2COOMe | 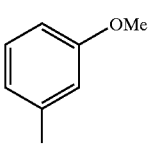 |

TABLE 60-continued
Formula LXI
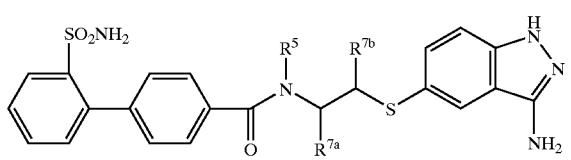
| R⁵ | R⁷ᵃ | R⁷ᵇ |
|---|---|---|
| Bn | —CH2CH2CONMe2 | 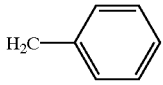 |
TABLE 61
Formula LXII
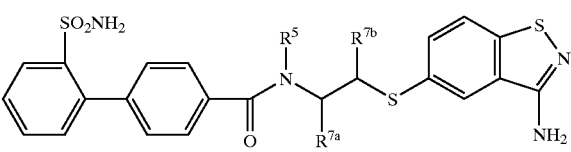
| R⁵ | R⁷ᵃ | R⁷ᵇ |
|---|---|---|
| H | H | H |
| Me | Me | H |
| 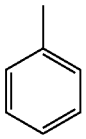 |  | Me |
| 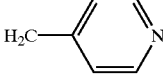 |  | Bn |
| 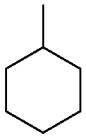 | 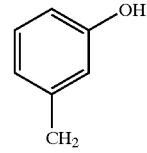 | 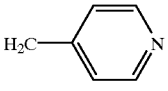 |
| 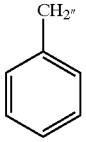 | 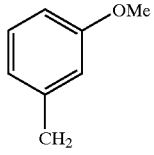 | 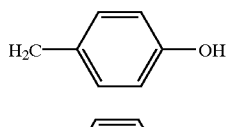 |
| H | —CH2OOH |  |
| Me | —CH2CH2COOMe | |

TABLE 61-continued
Formula LXII
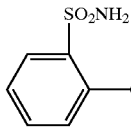
| R⁵ | R⁷ᵃ | R⁷ᵇ |
|---|---|---|
| Bn | —CH2CH2CONMe2 | 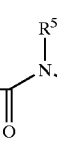 |
TABLE 62
Formula LXIII
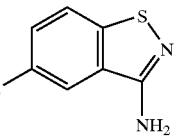
| R⁵ | R⁷ᵃ | R⁷ᵇ |
|---|---|---|
| H | H | H |
| Me | Me | H |
| 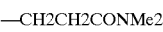 | 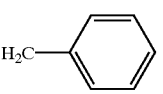 | Me |
| 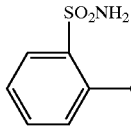 | 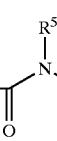 | Bn |
| 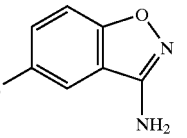 | 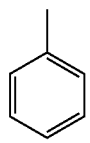 | 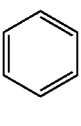 |
|  | 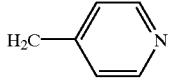 |  |
| H | —CH2OOH |  |
| Me | —CH2CH2COOMe | 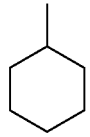 |

TABLE 62-continued
Formula LXIII
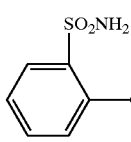
| R⁵ | R⁷ᵃ | R⁷ᵇ |
|---|---|---|
| Bn | —CH2CH2CONMe2 | 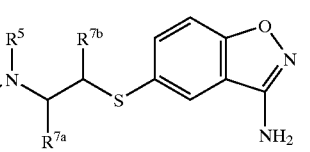 |
TABLE 63
Formula LXIV
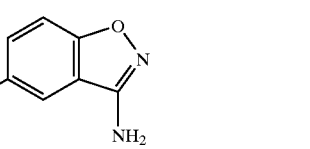
| R⁵ | R⁷ᵃ | R⁷ᵇ |
|---|---|---|
| H | H | H |
| Me | Me | H |
| 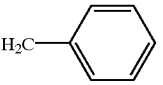 | 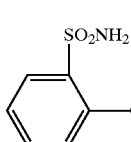 | Me |
| 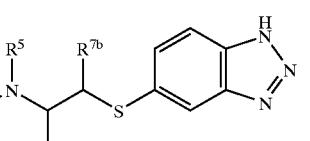 | 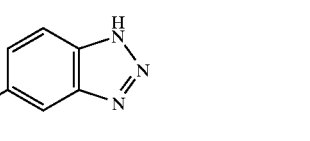 | Bn |
| 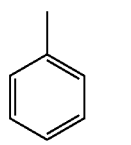 | 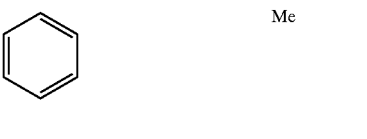 | 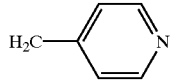 |
| 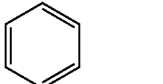 | 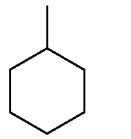 | 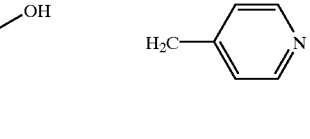 |
| H | —CH2OOH | 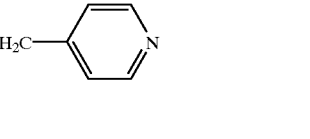 |
| Me | —CH2CH2COOMe | 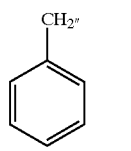 |

TABLE 63-continued
Formula LXIV
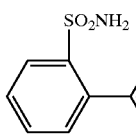
| R⁵ | R⁷ᵃ | R⁷ᵇ |
|---|---|---|
| Bn | —CH2CH2CONMe2 | 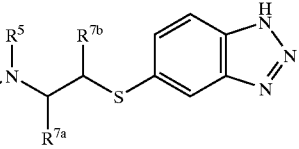 |
TABLE 64
Formula LXV
| R⁵ | R⁷ᵃ | R⁷ᵇ |
|---|---|---|
| H | H | H |
| Me | Me | H |
| 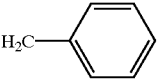 | 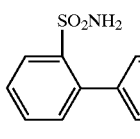 | Me |
| 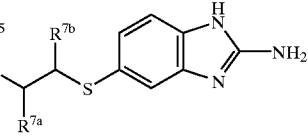 |  | Bn |
| 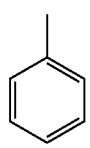 | 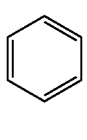 | 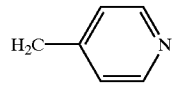 |
|  | 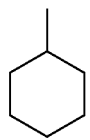 | 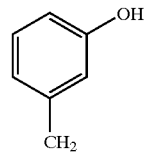 |
| H | —CH2OOH | 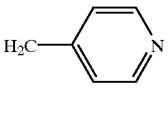 |
| Me | —CH2CH2COOMe | 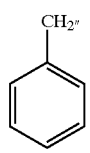 |

TABLE 64-continued
Formula LXV
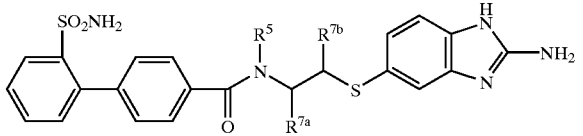
| R[5] | R[7a] | R[7b] |
|---|---|---|
| Bn | —CH2CH2CONMe2 | 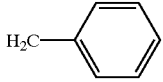 |
TABLE 65
Formula LXVI
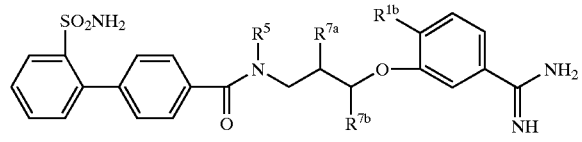
| R[5] | R[7a] | R[7b] | R[1b] |
|---|---|---|---|
| H | H | H | H |
| Me | Me | H | H |
| 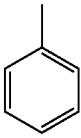 |  | Me | F |
| 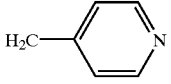 |  | Bn | OH |
| 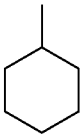 | 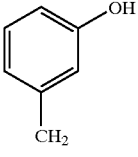 | 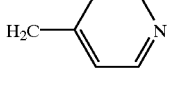 | OMe |
| 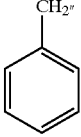 | 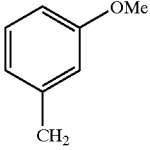 | 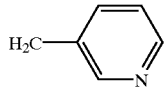 | OBn |
| H | —CH2OOH |  | OCH2COOH |
| Me | —CH2CH2COOMe |  | OCH2CH2OMe |

TABLE 65-continued
Formula LXVI
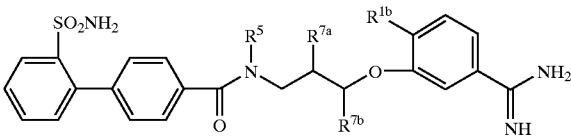
| R⁵ | R⁷ᵃ | R⁷ᵇ | R¹ᵇ |
|---|---|---|---|
| Bn | —CH2CH2CONMe2 | 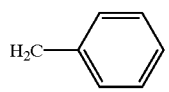 | OH |
TABLE 66
Formula LXVII
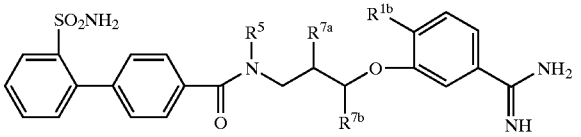
| R⁵ | R⁷ᵃ | R⁷ᵇ |
|---|---|---|
| H | H | H |
| Me | Me | H |
| 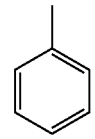 |  | Me |
| 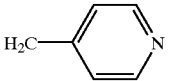 | 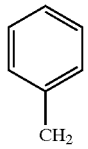 | Bn |
| 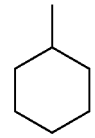 | 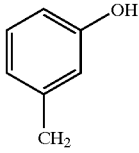 | 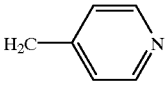 |
| 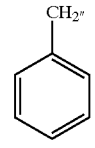 | 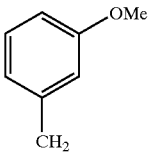 | 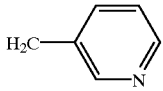 |
| H | —CH2OOH | 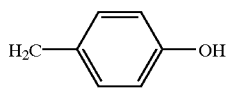 |
| Me | —CH2CH2COOMe | 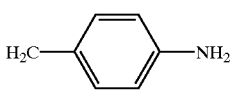 |

TABLE 66-continued

Formula LXVII

[Structure: 2-sulfamoylbiphenyl-4-carboxamide with N-R⁵, R⁷ᵃ, R⁷ᵇ substituents, connected via O to phenyl bearing R¹ᵇ and amidine (C(=NH)NH₂) group]

| R⁵ | R⁷ᵃ | R⁷ᵇ |
|---|---|---|
| Bn | —CH2CH2CONMe2 | H₂C–C₆H₅ (benzyl) |

TABLE 67

Formula LXVIII

[Structure: 2-sulfamoylbiphenyl-4-carboxamide with N-R⁵, R⁷ᵃ, R⁷ᵇ substituents, connected via O to 1-aminoisoquinolin-7-yl]

| R⁵ | R⁷ᵃ | R⁷ᵇ |
|---|---|---|
| H | H | H |
| Me | Me | H |
| | | Me |
| 4-methylphenyl (tolyl) | phenyl | |
| 4-pyridylmethyl (H₂C-4-pyridyl) | benzyl (CH₂-C₆H₅) | Bn |
| cyclohexyl | 3-hydroxybenzyl | 4-pyridylmethyl (H₂C-4-pyridyl) |
| benzyl (CH₂-C₆H₅) | 3-methoxybenzyl | 3-pyridylmethyl (H₂C-3-pyridyl) |
| H | —CH2OOH | 4-hydroxybenzyl (H₂C-C₆H₄-OH) |
| Me | —CH2CH2COOMe | 4-aminobenzyl (H₂C-C₆H₄-NH₂) |

TABLE 67-continued

Formula LXVIII

| R⁵ | R⁷ᵃ | R⁷ᵇ |
|---|---|---|
| Bn | —CH2CH2CONMe2 | benzyl (H₂C-Ph) |

TABLE 68

Formula LXVIX

| R⁵ | R⁷ᵃ | R⁷ᵇ |
|---|---|---|
| H | H | H |
| Me | Me | H |
| phenyl (tolyl-CH₂ group shown) | phenyl | Me |
| H₂C-(4-pyridyl) | benzyl (phenyl-CH₂) | Bn |
| cyclohexyl | 3-hydroxybenzyl (m-HO-C₆H₄-CH₂) | H₂C-(4-pyridyl) |
| benzyl (CH₂-Ph) | 3-methoxybenzyl (m-MeO-C₆H₄-CH₂) | H₂C-(3-pyridyl) |
| H | —CH2OOH | H₂C-(4-hydroxyphenyl) |
| Me | —CH2CH2COOMe | H₂C-(4-aminophenyl) |

TABLE 68-continued
Formula LXVIX
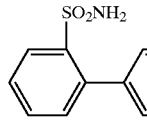
| R[5] | R[7a] | R[7b] |
|---|---|---|
| Bn | —CH2CH2CONMe2 | 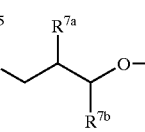 |
TABLE 69
Formula LXX
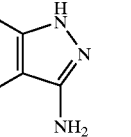
| R[5] | R[7a] | R[7b] |
|---|---|---|
| H | H | H |
| Me | Me | H |
|  | 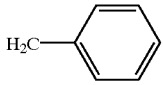 | Me |
| 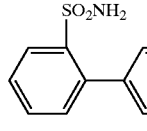 | 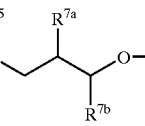 | Bn |
| 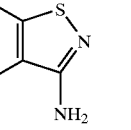 |  | 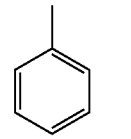 |
| 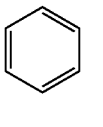 | 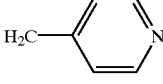 |  |
| H | —CH2OOH | 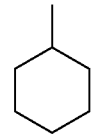 |
| Me | —CH2CH2COOMe | 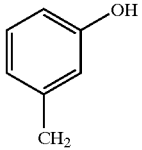 |

TABLE 69-continued
Formula LXX
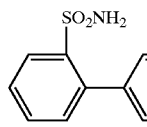
| R⁵ | R⁷ᵃ | R⁷ᵇ |
|---|---|---|
| Bn | —CH2CH2CONMe2 | 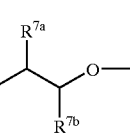 |
TABLE 70
Formula LXXI
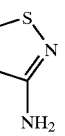
| R⁵ | R⁷ᵃ | R⁷ᵇ |
|---|---|---|
| H | H | H |
| Me | Me | H |
| 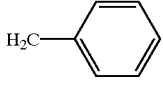 | 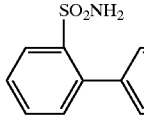 | Me |
| 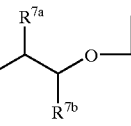 | 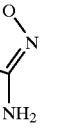 | Bn |
| 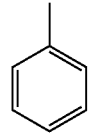 | 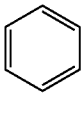 | 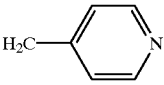 |
| 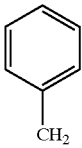 | 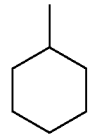 | 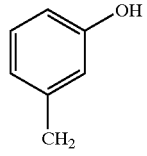 |
| H | —CH2OOH | 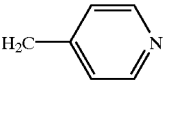 |
| Me | —CH2CH2COOMe | 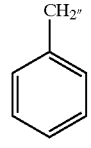 |

TABLE 70-continued
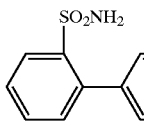
Formula LXXI
| R⁵ | R⁷ᵃ | R⁷ᵇ |
|---|---|---|
| Bn | —CH2CH2CONMe2 | 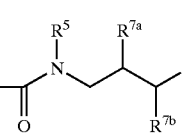 |
TABLE 71
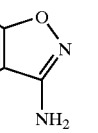
Formula LXXII
| R⁵ | R⁷ᵃ | R⁷ᵇ |
|---|---|---|
| H | H | H |
| Me | Me | H |
| 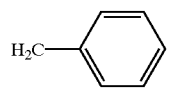 | 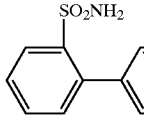 | Me |
| 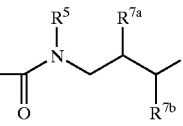 | 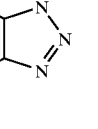 | Bn |
| 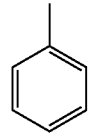 | 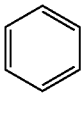 | 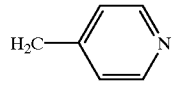 |
|  | 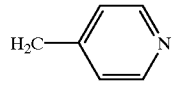 |  |
| H | —CH2OOH | 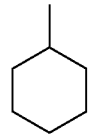 |
| Me | —CH2CH2COOMe | 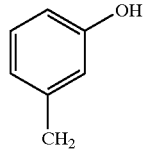 |

TABLE 71-continued

Formula LXXII

[Structure: 2-sulfamoyl-biphenyl-4-carboxamide N-substituted with R5, connected via CH2-C(R7a)-C(R7b)(O-benzotriazol-5-yl)]

| R⁵ | R⁷ᵃ | R⁷ᵇ |
|---|---|---|
| Bn | —CH2CH2CONMe2 | H2C—Ph |

TABLE 72

Formula LXXIII

[Structure: 2-sulfamoyl-biphenyl-4-carboxamide N-substituted with R5, connected via CH2-C(R7a)-C(R7b)(O-(2-amino-benzimidazol-5-yl))]

| R⁵ | R⁷ᵃ | R⁷ᵇ |
|---|---|---|
| H | H | H |
| Me | Me | H |
| 4-methylphenyl-CH2 (p-tolyl-CH2) | Ph | Me |
| H2C-(4-pyridyl) | Ph-CH2 (Bn) | Bn |
| cyclohexyl-CH2 | 3-HO-C6H4-CH2 | H2C-(4-pyridyl) |
| Bn (CH2-Ph) | 3-MeO-C6H4-CH2 | H2C-(3-pyridyl) |
| H | —CH2OOH | H2C-(4-HO-C6H4) |
| Me | —CH2CH2COOMe | H2C-(4-H2N-C6H4) |

TABLE 72-continued
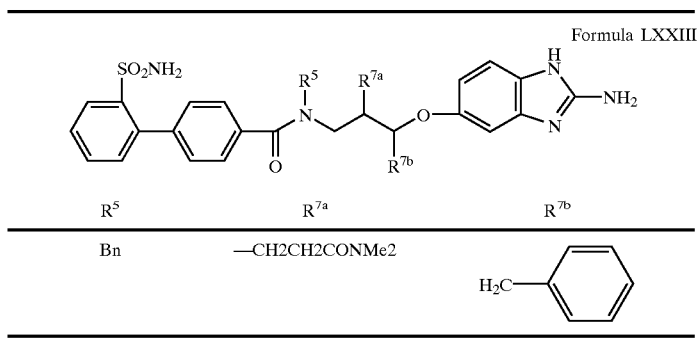
| $R^5$ | $R^{7a}$ | $R^{7b}$ |
|---|---|---|
| Bn | —CH2CH2CONMe2 | H₂C–phenyl |
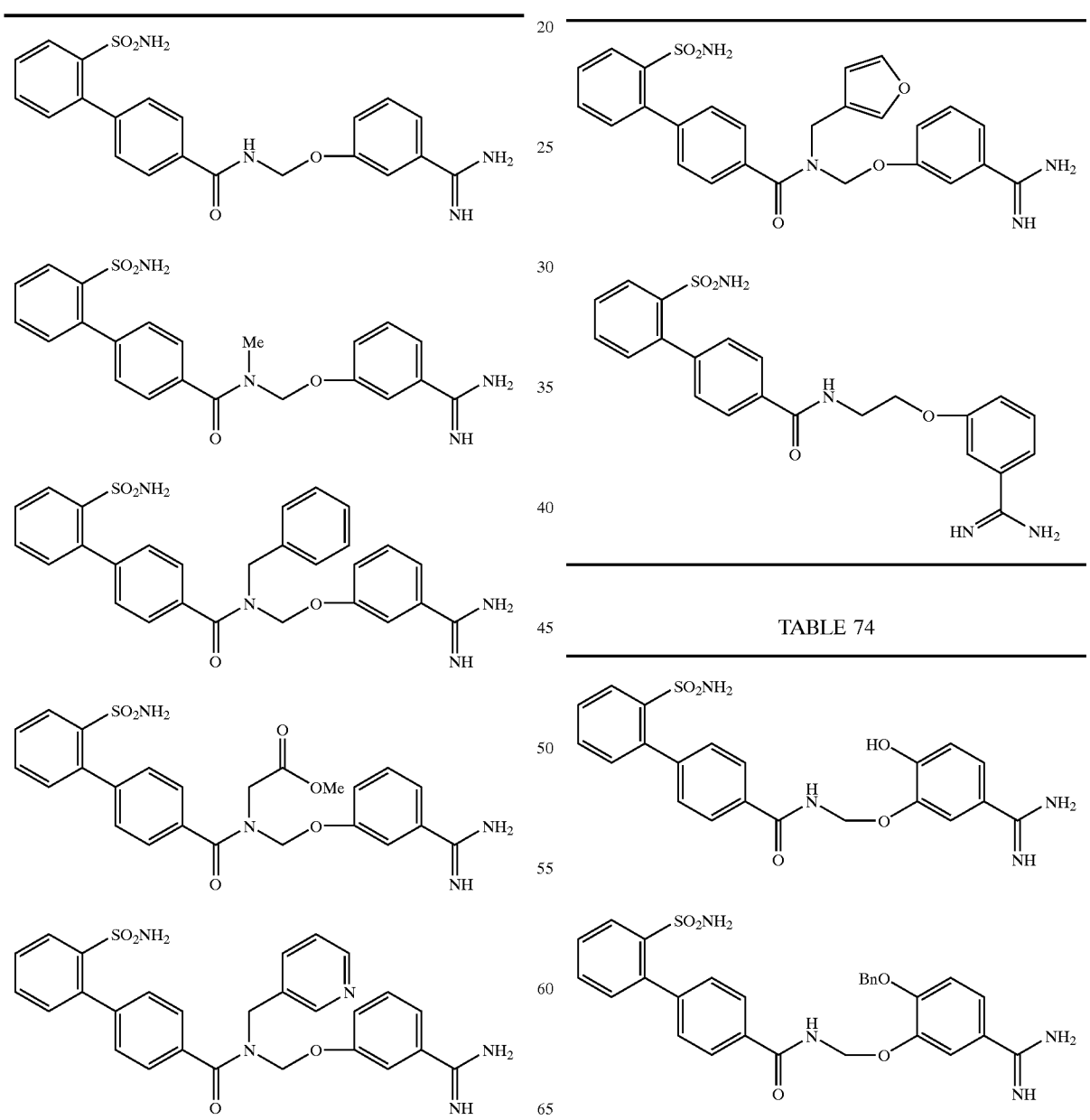

TABLE 74-continued

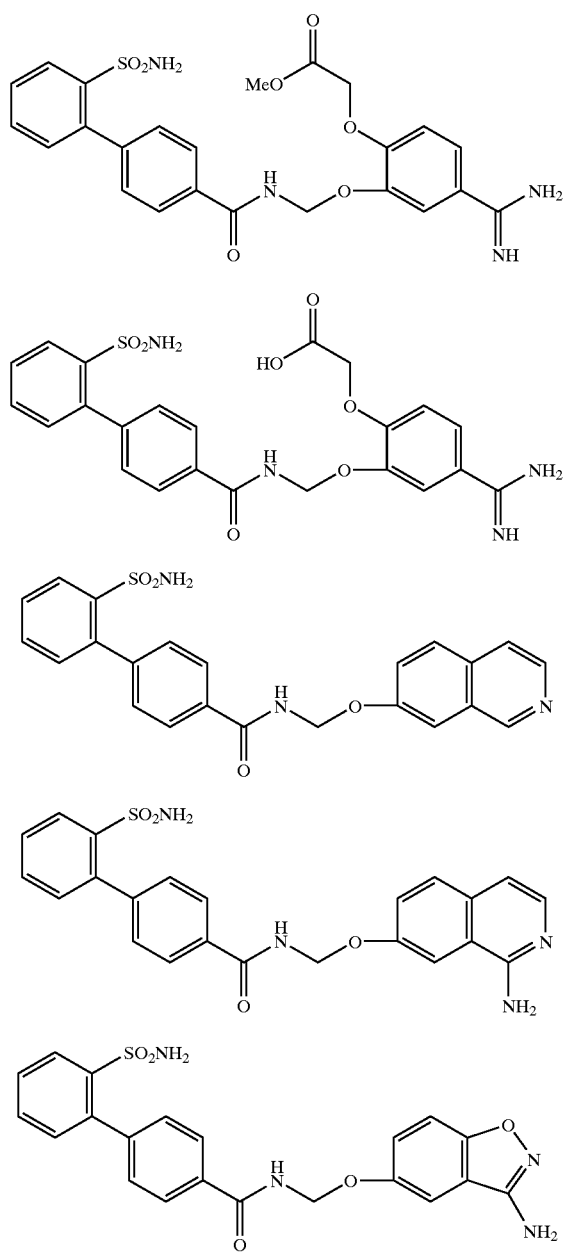

This invention also encompasses all pharmaceutically acceptable isomers, salts, hydrates and solvates of the compounds of formulas I, II and III. In addition, the compounds of formulas I, II and III can exist in various isomeric and tautomeric forms, and all such forms are meant to be included in the invention, along with pharmaceutically acceptable salts, hydrates and solvates of such isomers and tautomers.

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, the free acid or free base form of a compound of one of the formulas above can be reacted with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Prodrug Derivatives of Compounds

This invention also encompasses prodrug derivatives of the compounds contained herein. The term "prodrug" refers to a pharmacologically inactive derivative of a parent drug molecule that requires biotransformation, either spontaneous or enzymatic, within the organism to release the active drug. Prodrugs are variations or derivatives of the compounds of this invention which have groups cleavable under metabolic conditions. Prodrugs become the compounds of the invention which are pharmaceutically active in vivo, when they undergo solvolysis under physiological conditions or undergo enzymatic degradation. Prodrug compounds of this invention may be called single, double, triple etc., depending on the number of biotransformation steps required to release the active drug within the organism, and indicating the number of functionalities present in a precursor-type form. Prodrug forms often offer advantages of solubility, tissue compatibility, or delayed release in the mammalian organism (see, Bundgard, Design of Prodrugs, pp. 7–9, 21–24, Elsevier, Amsterdam 1985 and Silverman, The Organic Chemistry of Drug Design and Drug Action, pp. 352–401, Academic Press, San Diego, Calif., 1992). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

As mentioned above, the compounds of this invention find utility as therapeutic agents for disease states in mammals which have disorders of coagulation such as in the treatment or prevention of unstable angina, refractory angina, myocardial infarction, transient ischemic attacks, thrombotic stroke, embolic stroke, disseminated intravascular coagulation including the treatment of septic shock, deep venous thrombosis in the prevention of pulmonary embolism or the treatment of reocclusion or restenosis of reperfused coronary arteries. Further, these compounds are useful for the treatment or prophylaxis of those diseases which involve the production and/or action of factor Xa/prothrombinase complex. This includes a number of thrombotic and prothrombotic states in which the coagulation cascade is activated which include but are not limited to, deep venous thrombosis, pulmonary embolism, myocardial infarction, stroke, thromboembolic complications of surgery and peripheral arterial occlusion.

Accordingly, a method for preventing or treating a condition in a mammal characterized by undesired thrombosis comprises administering to the mammal a therapeutically effective amount of a compound of this invention. In addition to the disease states noted above, other diseases treatable or preventable by the administration of compounds of this invention include, without limitation, occlusive coronary thrombus formation resulting from either thrombolytic therapy or percutaneous transluminal coronary angioplasty, thrombus formation in the venous vasculature, disseminated intravascular coagulopathy, a condition wherein there is rapid consumption of coagulation factors and systemic coagulation which results in the formation of life-threatening thrombi occurring throughout the microvasculature leading to widespread organ failure, hemorrhagic stroke, renal dialysis, blood oxygenation, and cardiac catheterization.

The compounds of the invention also find utility in a method for inhibiting the coagulation biological samples, which comprises the administration of a compound of the invention.

The compounds of the present invention may also be used in combination with other therapeutic or diagnostic agents. In certain preferred embodiments, the compounds of this invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of the present invention may act in a synergistic fashion to prevent reocclusion following a successful thrombolytic therapy and/or reduce the time to reperfusion. These compounds may also allow for reduced doses of the thrombolytic agents to be used and therefore minimize potential hemorrhagic side-effects. The compounds of this invention can be utilized in vivo, ordinarily in mammals such as primates, (e.g. humans), sheep, horses, cattle, pigs, dogs, cats, rats and mice, or in vitro.

The biological properties of the compounds of the present invention can be readily characterized by methods that are well known in the art, for example by the in vitro protease activity assays and in vivo studies to evaluate antithrombotic efficacy, and effects on hemostasis and hematological parameters, such as are illustrated in the examples.

Diagnostic applications of the compounds of this invention will typically utilize formulations in the form of solutions or suspensions. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in Remington's Pharmaceutical Sciences, Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be 3–11, more preferably 5–9 and most preferably 7–8. It will be understood that use of certain of the foregoing excipients, carriers, or stabilizers will result in the formation of cyclic polypeptide salts. While the preferred route of administration is by injection, other methods of administration are also anticipated such as orally, intravenously (bolus and/or infusion), subcutaneously, intramuscularly, colonically, rectally, nasally, transdermally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of the invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidinone, pyran copolymer, polyhydroxypropyl-methacrylamide-phenol, polyhydroxyethyl-aspartamide-phenol, or polyethyleneoxide-polylysine substituted with palmitoyl residues. Furthermore, compounds of the invention may be coupled to a class of biodegradable polymers useful in achieving controlled release of a drug, for example polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the body's fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be readily determined by one skilled in the art. Typically, applications of compound are commenced at lower dosage levels, with dosage levels being increased until the desired effect is achieved.

The compounds of the invention can be administered orally or parenterally in an effective amount within the dosage range of about 0.1 to 100 mg/kg, preferably about 0.5 to 50 mg/kg and more preferably about 1 to 20 mg/kg on a regimen in a single or 2 to 4 divided daily doses and/or continuous infusion.

Typically, about 5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Preparation of Compounds

The compounds of the present invention may be synthesized by either solid or liquid phase methods described and referenced in standard textbooks, or by a combination of both methods. These methods are well known in the art. See, Bodanszky, "The Principles of Peptide Synthesis", Hafner, et al., Eds., Springer-Verlag, Berlin, 1984.

Starting materials used in any of these methods are commercially available from chemical vendors such as Aldrich, Sigma, Nova Biochemicals, Bachem Biosciences, and the like, or may be readily synthesized by known procedures.

Reactions are carried out in standard laboratory glassware and reaction vessels under reaction conditions of standard temperature and pressure, except where otherwise indicated.

During the synthesis of these compounds, the functional groups of the amino acid derivatives used in these methods are protected by blocking groups to prevent cross reaction during the coupling procedure. Examples of suitable blocking groups and their use are described in "The Peptides: Analysis, Synthesis, Biology", Academic Press, Vol. 3 (Gross, et al., Eds., 1981) and Vol. 9 (1987), the disclosures of which are incorporated herein by reference.

Non-limiting exemplary synthesis schemes are outlined directly below, and specific steps are described in the Examples. The reaction products are isolated and purified by conventional methods, typically by solvent extraction into a compatible solvent. The products may be further purified by column chromatography or other appropriate methods.

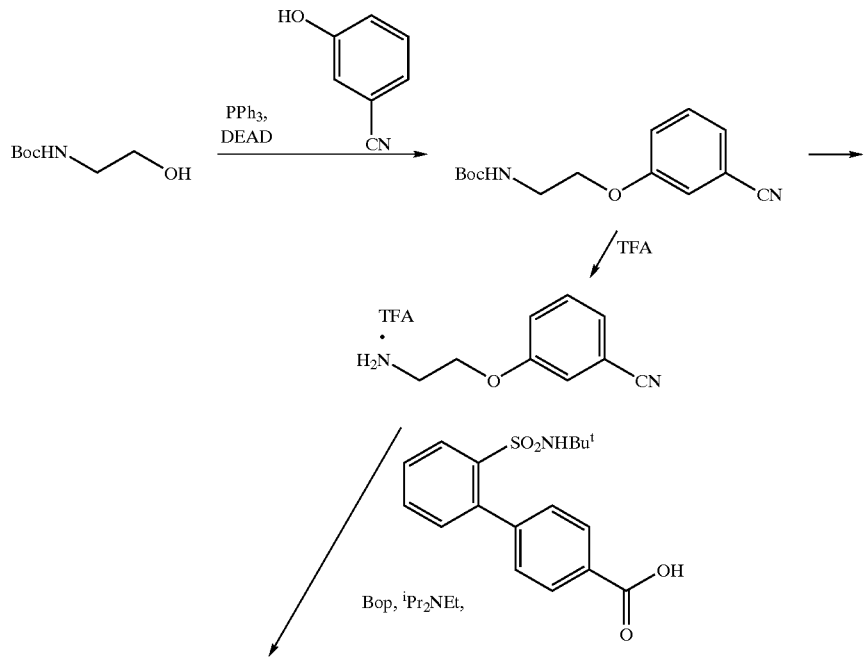

-continued
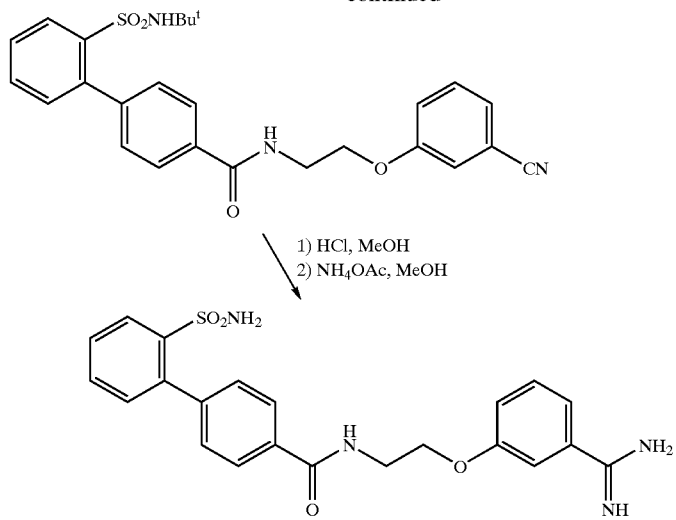
Scheme 2
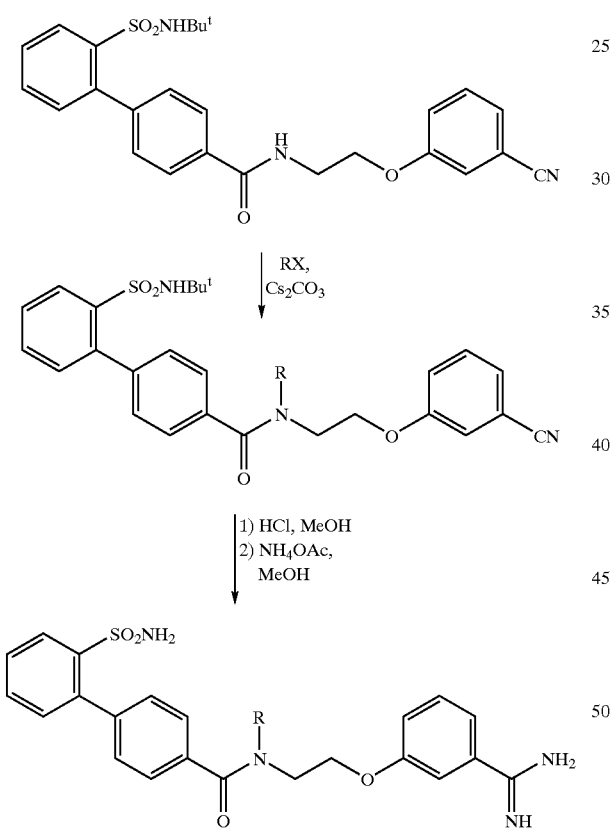
Scheme 3
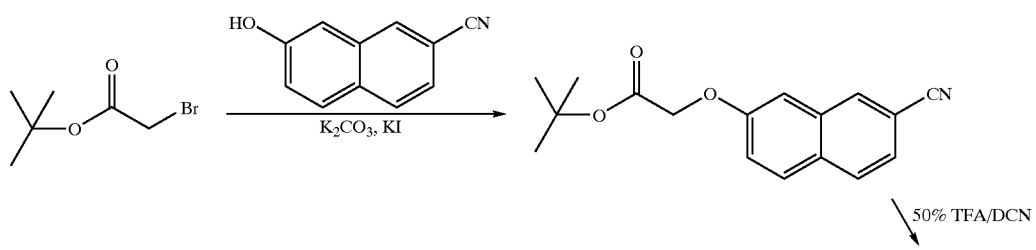

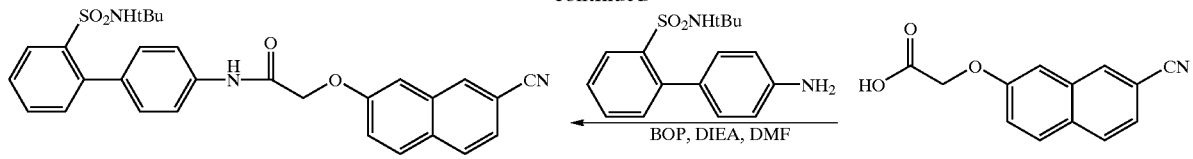
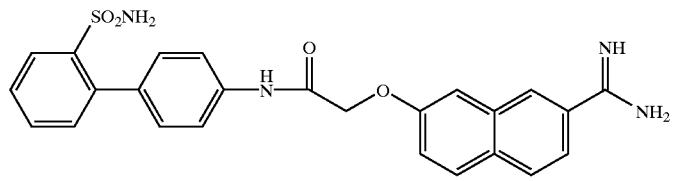
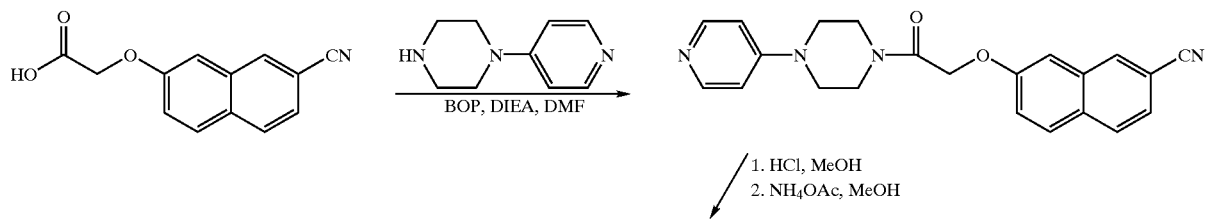
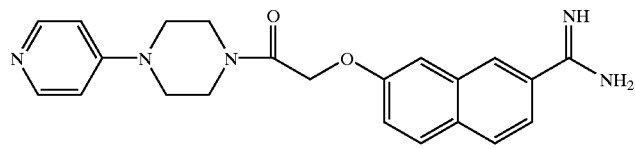
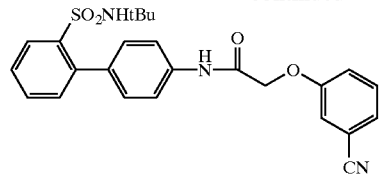
Scheme 4
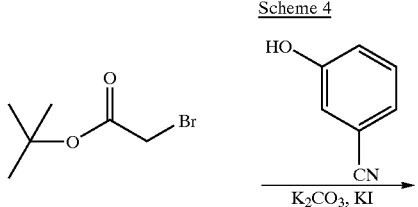
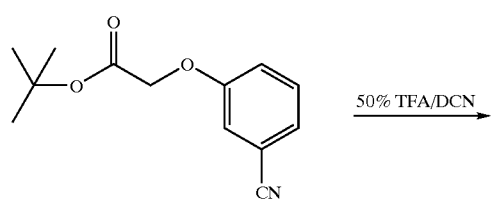
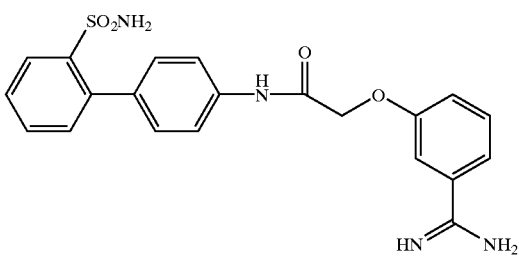
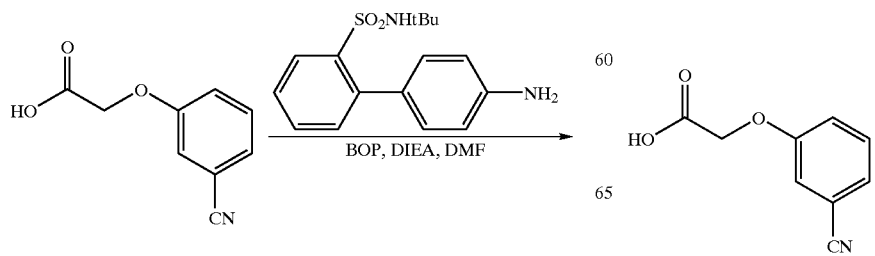
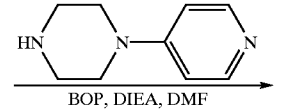

-continued

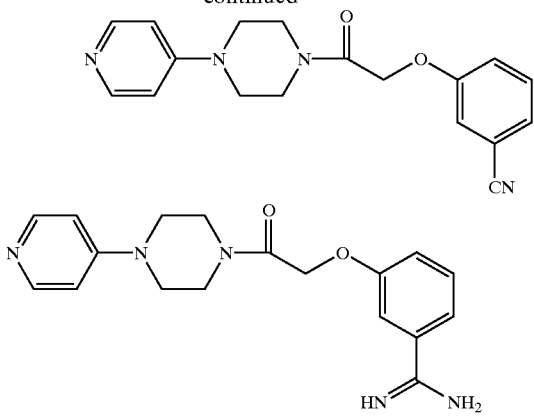

Compositions and Formulations

The compounds of this invention may be isolated as the free acid or base or converted to salts of various inorganic and organic acids and bases. Such salts are within the scope of this invention. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of the structures recited above with one or more molar equivalents of the desired acid or base in a solvent or solvent mixture in which the salt is insoluble, or in a solvent like water after which the solvent is removed by evaporation, distillation or freeze drying. Alternatively, the free acid or base form of the product may be passed over an ion exchange resin to form the desired salt or one salt form of the product may be converted to another using the same general process.

Diagnostic applications of the compounds of this invention will typically utilize formulations such as solution or suspension. In the management of thrombotic disorders the compounds of this invention may be utilized in compositions such as tablets, capsules or elixirs for oral administration, suppositories, sterile solutions or suspensions or injectable administration, and the like, or incorporated into shaped articles. Subjects in need of treatment (typically mammalian) using the compounds of this invention can be administered dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize.

Formulations of the compounds of this invention are prepared for storage or administration by mixing the compound having a desired degree of purity with physiologically acceptable carriers, excipients, stabilizers etc., and may be provided in sustained release or timed release formulations. Acceptable carriers or diluents for therapeutic use are well known in the pharmaceutical field, and are described, for example, in *Remington's Pharmaceutical Sciences,* Mack Publishing Co., (A. R. Gennaro edit. 1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinalpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as Tween, Pluronics or polyethyleneglycol.

Dosage formulations of the compounds of this invention to be used for therapeutic administration must be sterile. Sterility is readily accomplished by filtration through sterile membranes such as 0.2 micron membranes, or by other conventional methods. Formulations typically will be stored in lyophilized form or as an aqueous solution. The pH of the preparations of this invention typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by injection, other methods of administration are also anticipated such as intravenously (bolus and/or infusion), subcutaneously, intramuscularly, colonically, rectally, nasally or intraperitoneally, employing a variety of dosage forms such as suppositories, implanted pellets or small cylinders, aerosols, oral dosage formulations and topical formulations such as ointments, drops and dermal patches. The compounds of this invention are desirably incorporated into shaped articles such as implants which may employ inert materials such as biodegradable polymers or synthetic silicones, for example, Silastic, silicone rubber or other polymers commercially available.

The compounds of this invention may also be administered in the form of liposome delivery systems, such as small unilamellar vesicles, large unilamellar vesicles and multilamellar vesicles. Liposomes can be formed from a variety of lipids, such as cholesterol, stearylamine or phosphatidylcholines.

The compounds of this invention may also be delivered by the use of antibodies, antibody fragments, growth factors, hormones, or other targeting moieties, to which the compound molecules are coupled. The compounds of this invention may also be coupled with suitable polymers as targetable drug carriers. Such polymers can include polyvinylpyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the factor Xa inhibitors of this invention may be coupled to a class of biodegradable polymers useful in achieving controlled release of a drug, for example polylactic acid, polyglycolic acid, copolymers of polylactic and polyglycolic acid, poly-epsilon caprolactone, polyhydroxy butyric acid, polyorthoesters, polyacetals, polydihydropyrans, polycyanoacrylates and cross linked or amphipathic block copolymers of hydrogels. Polymers and semipermeable polymer matrices may be formed into shaped articles, such as valves, stents, tubing, prostheses and the like.

Therapeutic compound liquid formulations generally are placed into a container having a sterile access port, for example, an intravenous solution bag or vial having a stopper pierceable by hypodermic injection needle.

Therapeutically effective dosages may be determined by either in vitro or in vivo methods. For each particular compound of the present invention, individual determinations may be made to determine the optimal dosage required.

The range of therapeutically effective dosages will naturally be influenced by the route of administration, the therapeutic objectives, and the condition of the patient. For injection by hypodermic needle, it may be assumed the dosage is delivered into the body's fluids. For other routes of administration, the absorption efficiency must be individually determined for each inhibitor by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

Typically, about 0.5 to 500 mg of a compound or mixture of compounds of this invention, as the free acid or base form or as a pharmaceutically acceptable salt, is compounded with a physiologically acceptable vehicle, carrier, excipient, binder, preservative, stabilizer, dye, flavor etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin, and excipient such as microcrystalline cellulose, a disintegrating agent like corn starch or alginic acid, a lubricant such as magnesium stearate, a sweetening agent such as sucrose or lactose, or a flavoring agent. When a dosage form is a capsule, in addition to the above materials it may also contain a liquid carrier such as water, saline, a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

In practicing the methods of this invention, the compounds of this invention may be used alone or in combination, or in combination with other therapeutic or diagnostic agents. In certain preferred embodiments, the compounds of this inventions may be coadministered along with other compounds typically prescribed for these conditions according to generally accepted medical practice, such as anticoagulant agents, thrombolytic agents, or other antithrombotics, including platelet aggregation inhibitors, tissue plasminogen activators, urokinase, prourokinase, streptokinase, heparin, aspirin, or warfarin. The compounds of this invention can be utilized in vivo, ordinarily in mammals such as primates, such as humans, sheep, horses, cattle, pigs, dogs, cats, rats and mice, or in vitro.

The preferred compounds of the present invention are characterized by their ability to inhibit thrombus formation with acceptable effects on classical measures of coagulation parameters, platelets and platelet function, and acceptable levels of bleeding complications associated with their use. Conditions characterized by undesired thrombosis would include those involving the arterial and venous vasculature.

With respect to the coronary arterial vasculature, abnormal thrombus formation characterizes the rupture of an established atherosclerotic plaque which is the major cause of acute myocardial infarction and unstable angina, as well as also characterizing the occlusive coronary thrombus formation resulting from either thrombolytic therapy or percutaneous transluminal coronary angioplasty (PTCA).

With respect to the venous vasculature, abnormal thrombus formation characterizes the condition observed in patients undergoing major surgery in the lower extremities or the abdominal area who often suffer from thrombus formation in the venous vasculature resulting in reduced blood flow to the affected extremity and a predisposition to pulmonary embolism. Abnormal thrombus formation further characterizes disseminated intravascular coagulopathy commonly occurs within both vascular systems during septic shock, certain viral infections and cancer, a condition wherein there is rapid consumption of coagulation factors and systemic coagulation which results in the formation of life-threatening thrombi occurring throughout the microvasculature leading to widespread organ failure.

The compounds of this present invention, selected and used as disclosed herein, are believed to be useful for preventing or treating a condition characterized by undesired thrombosis, such as (a) the treatment or prevention of any thrombotically mediated acute coronary syndrome including myocardial infarction, unstable angina, refractory angina, occlusive coronary thrombus occurring post-thrombolytic therapy or post-coronary angioplasty, (b) the treatment or prevention of any thrombotically mediated cerebrovascular syndrome including embolic stroke, thrombotic stroke or transient ischemic attacks, (c) the treatment or prevention of any thrombotic syndrome occurring in the venous system including deep venous thrombosis or pulmonary embolus occurring either spontaneously or in the setting of malignancy, surgery or trauma, (d) the treatment or prevention of any coagulopathy including disseminated intravascular coagulation (including the setting of septic shock or other infection, surgery, pregnancy, trauma or malignancy and whether associated with multi-organ failure or not), thrombotic thrombocytopenic purpura, thromboangiitis obliterans, or thrombotic disease associated with heparin induced thrombocytopenia, (e) the treatment or prevention of thrombotic complications associated with extracorporeal circulation (e.g. renal dialysis, cardiopulmonary bypass or other oxygenation procedure, plasmapheresis), (f) the treatment or prevention of thrombotic complications associated with instrumentation (e.g. cardiac or other intravascular catheterization, intra-aortic balloon pump, coronary stent or cardiac valve), and (g) those involved with the fitting of prosthetic devices.

Anticoagulant therapy is also useful to prevent coagulation of stored whole blood and to prevent coagulation in other biological samples for testing or storage. Thus the compounds of this invention can be added to or contacted with any medium containing or suspected to contain factor Xa and in which it is desired that blood coagulation be inhibited, e.g., when contacting the mammal's blood with material such as vascular grafts, stents, orthopedic prostheses, cardiac stents, valves and prostheses, extra corporeal circulation systems and the like.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

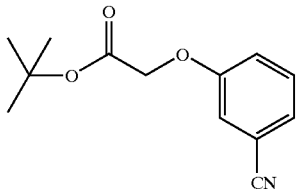

To a solution of t-butyl bromoacetate (1.62 mL, 10 mmol), 3-cyanophenol (1.19 g, 10 mmol), potassium carbonate (2.76 g, 20 mmol) in $CH_3CN$ (15 mL) and acetone (5 mL), was added KI (165 mg, 1 mmol). The mixture was heated to reflux for 2 hrs. The mixture was cooled to room temperature and solvent was removed in vacuo. Ether and water were added to the mixture and organic layer was washed with 2N NaOH, brine, dried over $Na_2SO_4$, filtered and the filtrated were concentrated in vacuo to give the title compound (2.53 g, 100%). ES-MS (M+H)+=234.1

Example 2

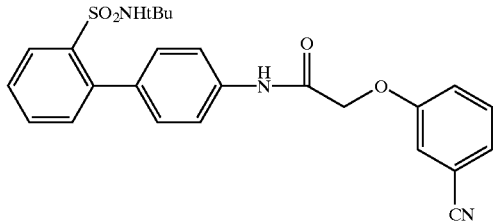

The compound of example 1 (0.3 mmol) was treated with 50% TFA in DCM (4 mL). The mixture was stirred at room temperature for 30 minutes and solvent evaporated to give a white solid. This was dissolved in DMF (2 mL) and cooled to 0° C. The solution was neutralized with DIEA (87 μL, 0.5 mmol) followed by the addition of compound of example 4 (76 mg, 0.25 mmol) and coupling reagent BOP(132.8 mg, 0.3 mmol). The solution was stirred at room temperature for 15 hours. The reaction mixture was diluted in a mixture of EtOAc/$H_2O$ (10 mL:5mL). The organic layer was washed with sat. $NaHCO_3$ (2×10 mL), sat. NaCl (2×10 nL), dried over $MgSO_4$, filtered and solvent evaporated to give the crude product. This was purified by silica gel column chromatography using solvent system 50% EtOAc in hexane as eluant to give the title compound (121 mg, 100%). ES-MS (M+Na)+=486.15.

Example 3

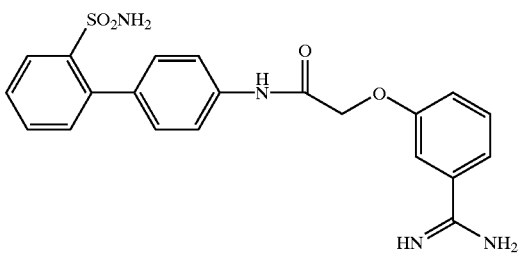

A solution of the compound of example 2 (121 mg, 0.26 mmol), hydroxylamine hydrochloride (36.14 mg, 0.52 mmol), TEA (109 μL, 0.78 mmol) in absolute ethanol (4 mL) was heated up to 60° C. and stirred for 15 hrs. The solution was cooled and solvent evaporated. The residue was dissolved in AcOH (2 mL). $Ac_2O$ (98.5 μL, 1.04 mmol) was added. The mixture was stirred at room temperature for 50 min. and the solvent evaporated. The residue was dissolved in MeOH (2–3 mL) and 10% Pd/C (catalytic amount) was added. The mixture was hydrogenated under balloon overnight, filtered through Celite to remove the catalyst and the filtrate was evaporated. TFA (2–3 mL) was added to the residue and the mixture was stirred at room temperature for 2–3 hrs. TFA was removed under reduced pressure to give the crude product. The obtained residue was purified by RP-HPLC to give the title compound as a white powder. ES-MS (M+H)+=425.1.

Example 4

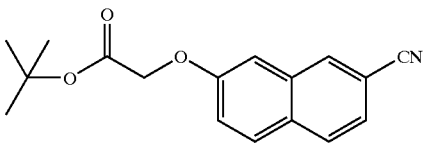

To a solution 6 of t-butyl bromoacetate (1.62 mL, 10 mmol), 7-cyano-2-naphthol (1.69 g, 10 mmol), potassium carbonate (2.76 g, 20 mmol) in $CH_3CN$ (15 mL) and acetone (5 mL), was added KI (165 mg, 1 mmol). The mixture was heated to reflux for 2 hrs. The mixture was cooled to room temperature and solvent was removed in vacuo. Ether and water were added to the mixture and organic layer was washed with 2N NaOH, brine, dried over $Na_2SO_4$, filtered and the filtrated were concentrated in vacuo to give the title compound (2.76 g, 97.5%). ES-MS (M+H)+=284.1.

Example 5

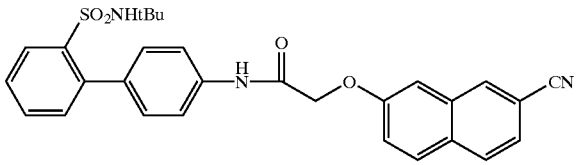

The compound of example 4 (0.3 mmol) was treated with 50% TFA in DCM (4 mL). The mixture was stirred at room temperature for 30 minutes and solvent evaporated to give a white solid. This was dissolved in DMF (2 mL) and cooled to 0° C. The solution was neutralized with DIEA (87 μL, 0.5 mmol) followed by the addition of compound of example 4 (76 mg, 0.25 mmol) and coupling reagent BOP(132.8 mg, 0.3 mmol). The solution was stirred at room temperature for 15 hours. The reaction mixture was diluted in a mixture of EtOAc/H$_2$O (10 mL:5mL). The organic layer was washed with sat. NaHCO$_3$ (2×10 mL), sat. NaCl (2×10 mL), dried over MgSO$_4$, filtered and solvent evaporated to give the crude product. This was purified by silica gel column chromatography using solvent system 50% EtOAc in hexane as eluant to give the title compound (142 mg, 92.2%). ES-MS (N+Na)+=536.15.

Example 6

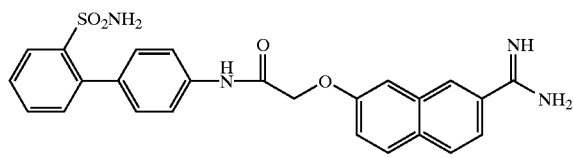

A solution of the compound of example 5 (142 mg, 0.28 mmol), hydroxylamine hydrochloride (38.5 mg, 0.55 mmol), TEA (115 µL, 0.83 mmol) in absolute ethanol (4 mL) was heated up to 60° C. and stirred for 15 hrs. The solution was cooled and solvent evaporated. The residue was dissolved in AcOH (2 mL). Ac$_2$O (104 µL, 1.11 mmol) was added. The mixture was stirred at room temperature for 50 min. and the solvent evaporated. The residue was dissolved in MeOH (2–3 mL) and 10% Pd/C (catalytic amount) was added. The mixture was hydrogenated under balloon overnight, filtered through Celite to remove the catalyst and the filtrate was evaporated. TFA (2–3 mL) was added to the residue and the mixture was stirred at room temperature for 2–3 hrs. TFA was removed under reduced pressure to give the crude product. The obtained residue was purified by RP-HPLC to give the title compound as a white powder. ES-MS (M+H)+=475.1.

Example 7

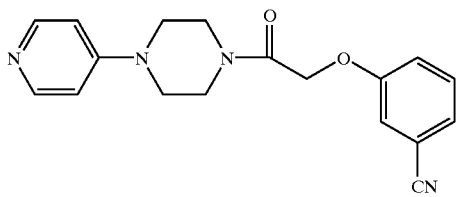

The compound of example 1(1 mmol) was treated with 50% TFA in DCM (4 mL). The mixture was stirred at room temperature for 30 minutes and solvent evaporated to give a white solid. This was dissolved in DMF (8 mL) and cooled to 0° C. The solution was neutralized with DIEA (349 µL, 2 mmol) followed by the addition of 1-(4-pyridyl)-piperazine (194 mg, 1.2 mmol) and coupling reagent BOP(531 mg, 1.2 mmol). The solution was stirred at room temperature for 15 hours. The reaction mixture was diluted in a mixture of EtOAc/H$_2$O (10 mL:5mL). The organic layer was washed with sat. NaHCO$_3$ (2×10 mL), sat. NaCl (2×10 mL), dried over MgSO$_4$, filtered and solvent evaporated to give the title compound (132 mg, 41%). ES-MS (M+H)+=322.1.

Example 8

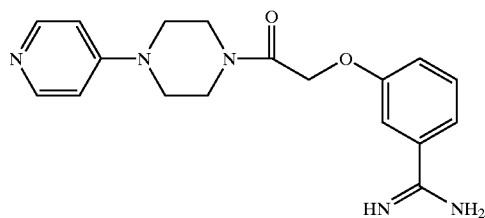

A solution of the compound of example 7 (132 mg, 0.41 mmol) in MeOH (3 mL) was treated with a stream of HCl gas for 10 min. at 0° C. The resulting solution was capped, stirred at room temperature overnight and evaporated in vacuo. The residue was reconstituted in MeOH (3 mL) and the mixture was treated with NH$_4$OAc (142.6 mg, 1.85 mmol). The reaction mixture was refluxed for 1.5 hrs. and concentrated in vacuo. The obtained residue was purified by RP-HPLC to give the title compound as a white powder. ES-MS (M+H)+=340.1.

Example 9

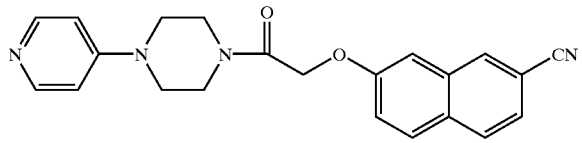

The compound of example 4 (1 mmol) was treated with 50% TFA in DCM (4 mL). The mixture was stirred at room temperature for 30 minutes and solvent evaporated to give a white solid. This was dissolved in DMF (8 mL) and cooled to 0° C. The solution was neutralized with DIEA (349 µL, 2 mmol) followed by the addition of 1-(4-pyridyl)-piperazine (194 mg, 1.2 mmol) and coupling reagent BOP(531 mg, 1.2 mmol). The solution was stirred at room temperature for 15 hours. The reaction mixture was diluted in a mixture of EtOAc/H$_2$O (10 mL: 5mL). The organic layer was washed with sat. NaHCO$_3$ (2×10 mL), sat. NaCl (2×10 mL), dried over MgSO$_4$, filtered and solvent evaporated to give the title compound (209 mg, 56.3%). ES-MS (M+H)+=372.1.

Example 10

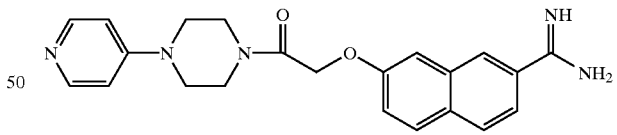

A solution compound of example 9 (113 mg, 0.3 mmol) in MEOH (3 mL) was treated with a stream of HCl gas for 10 min. at 0° C. The resulting solution was capped, stirred at room temperature overnight and evaporated in vacuo. The residue was reconstituted in MeOH (3 mL) and the mixture was treated with NH$_4$OAc (115.6 mg, 1.5 mmol). The reaction mixture was refluxed for 1.5 hrs. and concentrated in vacuo. The obtained residue was purified by RP-HPLC to give the title compound as a white powder. ES-MS (M+H)+=390.1.

Biological Activity Examples

Evaluation of the compounds of this invention is guided by in vitro protease activity assays (see below) and in vivo studies to evaluate antithrombotic efficacy, and effects on hemostasis and hematological parameters.

The compounds of the present invention are dissolved in buffer to give solutions containing concentrations such that assay concentrations range from 0 to 100 μM. In the assays for thrombin, prothrombinase and factor Xa, a synthetic chromogenic substrate is added to a solution containing test compound and the enzyme of interest and the residual catalytic activity of that enzyme is determined spectrophotometrically. The $IC_{50}$ of a compound is determined from the substrate turnover. The $IC_{50}$ is the concentration of test compound giving 50% inhibition of the substrate turnover. The compounds of the present invention desirably have an $IC_{50}$ of less than 500 nM in the factor Xa assay, preferably less than 200 nM, and more preferred compounds have an $IC_{50}$ of about 100 nM or less in the factor Xa assay. The compounds of the present invention desirably have an $IC_{50}$ of less than 4.0 μM in the prothrombinase assay, preferably less than 200 nM, and more preferred compounds have an $IC_{50}$ of about 10 nM or less in the prothrombinase assay. The compounds of the present invention desirably have an $IC_{50}$ of greater than 1.0 μM in the thrombin assay, preferably greater than 10.0 μM, and more preferred compounds have an $IC_{50}$ of greater than 100.0 μM in the thrombin assay.

Amidolytic Assays for Determining Protease Inhibition Activity

The factor Xa and thrombin assays are performed at room temperature, in 0.02 M Tris·HCl buffer, pH 7.5, containing 0.15 M NaCl. The rates of hydrolysis of the para-nitroanilide substrate S-2765 (Chromogenix) for factor Xa, and the substrate Chromozym TH (Boehringer Mannheim) for thrombin following preincubation of the enzyme with inhibitor for 5 minutes at room temperature, and were determined using the Softmax 96-well plate reader (Molecular Devices), monitored at 405 nm to measure the time dependent appearance of p-nitroaniline.

The prothrombinase inhibition assay is performed in a plasma free system with modifications to the method described by Sinha, U. et al., Thromb. Res., 75, 427–436 (1994). Specifically, the activity of the prothrombinase complex is determined by measuring the time course of thrombin generation using the p-nitroanilide substrate Chromozym TH. The assay consists of preincubation ( 5 minutes) of selected compounds to be tested as inhibitors with the complex formed from factor Xa (0.5 nM), factor Va (2 nM), phosphatidyl serine:phosphatidyl choline (25:75, 20 μM) in 20 mM Tris·HCl buffer, pH 7.5, containing 0.15 M NaCl, 5 mM $CaCl_2$ and 0.1% bovine serum albumin. Aliquots from the complex-inhibitor mixture are added to prothrombin (1 nM) and Chromozym TH (0.1 mM). The rate of substrate cleavage is monitored at 405 nm for two minutes. Eight different concentrations of inhibitor are assayed in duplicate. A standard curve of thrombin generation by an equivalent amount of untreated complex are used for determination of percent inhibition.

Antithrombotic Efficacy in a Rabbit Model of Venous Thrombosis

A rabbit deep vein thrombosis model as described by Hollenbach, S. et al., Thromb. Haemost. 71, 357–362 (1994), is used to determine the in-vivo antithrombotic activity of the test compounds. Rabbits are anesthetized with I.M. injections of Ketamine, Xylazine, and Acepromazine cocktail. A standardized protocol consists of insertion of a thrombogenic cotton thread and copper wire apparatus into the abdominal vena cava of the anesthetized rabbit. A non-occlusive thrombus is allowed to develop in the central venous circulation and inhibition of thrombus growth is used as a measure of the antithrombotic activity of the studied compounds. Test agents or control saline are administered through a marginal ear vein catheter. A femoral vein catheter is used for blood sampling prior to and during steady state infusion of test compound. Initiation of thrombus formation begins immediately after advancement of the cotton thread apparatus into the central venous circulation. Test compounds are administered from time=30 min to time=150 min at which the experiment is terminated. The rabbits are euthanized and the thrombus excised by surgical dissection and characterized by weight and histology. Blood samples are analyzed for changes in hematological and coagulation parameters.

Effects of Compounds in Rabbit Venous Thrombosis Model

Administration of compounds in the rabbit venous thrombosis model demonstrates antithrombotic efficacy at the higher doses evaluated. There are no significant effects of the compound on the aPTT and PT prolongation with the highest dose (100 μg/kg+2.57 μg/kg/min). Compounds have no significant effects on hematological parameters as compared to saline controls. All measurements are an average of all samples after steady state administration of vehicle or (D)-Arg-Gly-Arg-thiazole. Values are expressed as mean±SD.

Without further description, it is believed that one of ordinary skill in the art can, using the preceding description and the following illustrative examples, make and utilize the compounds of the present invention and practice the claimed methods.

What is claimed is:

1. A compound according to the formula:

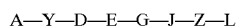

wherein:

A is selected from the group consisting of:
(a) $C_3$–$C_8$-cycloalkyl;
(b) phenyl, which is independently substituted with 0–2 $R^1$ substituents; and
(c) naphthyl, which is independently substituted with 0–2 $R^1$ substituents;

$R^1$ is selected from the group consisting of:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —$NO_2$, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_1$–$C_4$-alkyl, —CN, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl and —$NO_2$;

$R^2$ and $R^3$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalky, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —$NO_2$;

m is an integer of 0–2;

Y is a direct link;

D is a member selected from the group consisting of:
(a) phenyl, which is independently substituted with 0–2 $R^{1a}$ substituents; and
(b) naphthyl, which is independently substituted with 0–2 $R^{1a}$ substituents;

$R^{1a}$ is selected from the group consisting of:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, —NO$_2$, $(CH_2)_m NR^{2a}R^{3a}$, $SO_2NR^{2a}R^{3a}$, $SO_2R^{2a}$, $CF_3$, $OR^{2a}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

$R^{2a}$ and $R^{3a}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

E is —N($R^5$)—C(=O)—;

$R^5$ is selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl, wherein from 1–4 hydrogen atoms on the ring atoms of the phenyl, naphthyl and heteroaryl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_3$cycloalkyl, —CN and —NO$_2$;

G is selected from the group consisting of:
—$CR^7R^8$— and —$CR^{7a}R^{8a}$—$CR^{7b}R^{8b}$—
wherein $R^7$, $R^8$, $R^{7a}$, $R^{8a}$, $R^{7b}$ and $R^{8b}$ are independently a member selected from the group consisting of:
hydrogen, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, $C_{0-4}$alkylphenyl, $C_{0-4}$alkylnaphthyl, $C_{0-4}$alkylimidazolyl, —$OR^9$, —$C_{0-4}$alkylCOO$R^9$, —$C_{0-4}$alkylC(=O)N$R^9R^{10}$, —$C_{0-4}$alkylC(=O)N$R^9$—$CH_2$—$CH_2$—O—$R^{10}$, —$C_{0-4}$alkylC(=O)N$R^9$(—$CH_2$—$CH_2$—O—$R^{10}$—)$_2$, —N($R^9$)COR$^{10}$, —N($R^9$)C(=O)$R^{10}$, —N($R^9$)SO$_2R^{10}$, and a naturally occurring or synthetic amino acid side chain, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN, —OH, —O$C_{1-4}$alkyl, —O$C_{1-4}$alkyl-OMe, —OCH$_2$COOH, and —NO$_2$;

$R^9$ and $R^{10}$ are independently selected from the group consisting of:
H, $C_{1-4}$alkyl, $C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl-$C_{3-8}$cycloalkyl, —CN and —NO$_2$, and wherein $R^9$ and $R^{10}$ taken together can form a 5–8 membered heterocylic ring;

J is —O—;

Z is a member selected from the group consisting of:
(a) phenyl, which is independently substituted with 0–2 $R^{1b}$ substituents; and
(b) naphthyl, which is independently substituted with 0–2 $R^{1b}$ substituents;

$R^{1b}$ is selected from the group consisting of:
Halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, NO$_2$, NR$^{2b}R^{3b}$, SO$_2$NR$^{2b}R^{3b}$, SO$_2R^{2b}$, CF$_3$, OR$^{2b}$, O—CH$_2$—OPh, O—CH$_2$—Ph, O—CH$_2$CH$_2$—OR$^{2b}$, O—CH$_2$—COOR$^{2b}$, N($R^{2b}$)—CH$_2$—CH$_2$—OR$^{2b}$, N(—CH$_2$—CH$_2$—OR$^{2b}$)$_2$, N($R^{2b}$)—C(=O)$R^{3b}$, N($R^{2b}$)—SO$_2$—$R^{3b}$, and a 5–6 membered aromatic heterocyclic system containing from 1–4 heteroatoms selected from the group consisting of N, O and S, wherein from 1–4 hydrogen atoms on the aromatic heterocyclic system may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

$R^{2b}$ and $R^{3b}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN and —NO$_2$;

L is C(=N$R^{12}$)N$R^{12}$ $R^{13}$;

$R^{12}$ and $R^{13}$ are independently selected from the group consisting of:
hydrogen, —$OR^{14}$, —$NR^{14}R^{15}$, $C_{1-4}$alkyl, $C_{0-4}$alkylphenyl, $C_{0-4}$alkylnaphthyl, COO$C_{1-4}$alkyl, COO—$C_{0-4}$alkylphenyl and COO—$C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

$R^{14}$ and $R^{15}$ are independently selected from the group consisting of:
H, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, $C_{0-4}$alkylphenyl and $C_{0-4}$alkylnaphthyl, wherein from 1–4 hydrogen atoms on the ring atoms of the phenyl and naphthyl moieties may be independently replaced with a member selected from the group consisting of halo, $C_{1-4}$alkyl, $C_{2-6}$alkenyl, $C_{2-6}$alkynyl, $C_{3-8}$cycloalkyl, $C_{0-4}$alkyl$C_{3-8}$cycloalkyl, —CN, and —NO$_2$;

and all pharmaceutically acceptable isomers, salts, hydrates, solvates and prodrug derivatives thereof.

2. A compound of claim 1, wherein:

A is selected from the group consisting of:
  (a) $C_3$–$C_8$-cycloalkyl;
  (b) phenyl, which is independently substituted with 0–2 $R^1$ substituents; and
  (c) naphthyl, which is independently substituted with 0–2 $R^1$ substituents;

$R^1$ is selected from the group consisting of:
  halo, $C_{1-4}$alkyl, —CN, $(CH_2)_m NR^2 R^3$, $SO_2 NR^2 R^3$, $SO_2 R^2$, $CF_3$, $OR^2$, and a 5–6 membered aromatic heterocyclic system containing from 1–4 heteroatoms selected from the group consisting of N, O and S;

$R^2$ and $R^3$ are independently selected from the group consisting of:
  H, $C_{1-4}$alkyl, $C_{0-4}$alkylphenyl and $C_{0-4}$alkylnaphthyl;

m is an integer of 0–2;

Y is a direct link;

D is a member selected from the group consisting of:
  (a) phenyl, which is independently substituted with 0–2 $R^{1a}$ substituents; and
  (b) naphthyl, which is independently substituted with 0–2 $R^{1a}$ substituents;

$R^{1a}$ is selected from the group consisting of:
  Halo, $C_{1-4}$alkyl, —CN, —$NO_2$, $(CH_2)_m NR^{2a} R^{3a}$, $SO_2 NR^{2a} R^{3a}$, $SO_2 R^{2a}$, $CF_3$, $OR^{2a}$, and a 5–6 membered aromatic heterocyclic ring containing from 1–4 heteroatoms selected from the group consisting of N, O and S;

$R^{2a}$ and $R^{3a}$ are independently selected from the group consisting of:
  H, $C_{1-4}$alkyl, $C_{0-4}$alkylphenyl and $C_{0-4}$alkylnaphthyl;

E is —N($R^5$)—C(=O)—;

$R^5$ is selected from the group consisting of:
  H, $C_{1-4}$alkyl, $C_{0-4}$alkylphenyl, $C_{0-4}$alkylnaphthyl, $C_{0-4}$alkylheteroaryl, $C_{1-4}$alkylCOOH and $C_{1-4}$alkylCOO$C_{1-4}$alkyl;

G is selected from the group consisting of:
  —$CR^7 R^8$— and —$CR^{7a} R^{8a}$—$CR^{7b} R^{8b}$— wherein $R^7$, $R^8$, $R^{7a}$, $R^{8a}$, $R^{7b}$ and $R^{8b}$ are independently a member selected from the group consisting of:
  hydrogen, $C_{1-4}$alkyl, $C_{0-4}$alkyl-$C_{3-8}$cycloalkyl, $C_{0-4}$alkylphenyl, $C_{0-4}$alkylnaphthyl, —$OR^9$, —$C_{0-4}$alkylCOO$R^9$, —$C_{0-4}$alkylC(=O)N$R^9 R^{10}$, —N($R^9$)CO$R^{10}$, —N($R^9$)C(=O)$R^{10}$, —N($R^9$)$SO_2 R^{10}$, and common amino acid side chains;

$R^9$ and $R^{10}$ are independently selected from the group consisting of:
  H, $C_{1-4}$alkyl, $C_{0-4}$alkylphenyl and $C_{0-4}$alkylnaphthyl;

J is —O—;

Z is a member selected from the group consisting of:
  (a) phenyl, which is independently substituted with 0–2 $R^{1b}$ substituents; and
  (b) naphthyl, which is independently substituted with 0–2 $R^{1b}$ substituents;

$R^{1b}$ is selected from the group consisting of:
  halo, $C_{1-4}$alkyl, —CN, —$NO_2$, $NR^{2b} R^{3b}$, $SO_2 NR^{2b} R^{3b}$, $SO_2 R^{2b}$, $CF_3$, $OR^{2b}$, O—$CH_2$—$CH_2$—$OR^{2b}$, O—$CH_2$—COO$R^{2b}$, N($R^{2b}$)—$CH_2$—$CH_2$—$OR^{2b}$, N(—$CH_2$—$CH_2$—$OR^{2b}$)$_2$, N($R^{2b}$)—C(=O)$R^{3b}$, N($R^{2b}$)—$SO_2$—$R^{3b}$, and a 5–6 membered aromatic heterocyclic ring containing from 1–4 heteroatoms selected from the group consisting of N, O and S;

$R^{2b}$ and $R^{3b}$ are independently selected from the group consisting of:
  H, $C_{1-4}$alkyl, $C_{0-4}$alkylphenyl and $C_{0-4}$alkylnaphthyl;

L is C(=$NR^{12}$)$NR^{12} R^{13}$;

$R^{12}$ and $R^{13}$ are independently selected from the group consisting of:
  hydrogen, —$OR^{14}$, —$NR^{14} R^{15}$, $C_{1-4}$alkyl, $C_{0-4}$alkylphenyl, $C_{0-4}$alkylnaphthyl, COO$C_{1-4}$alkyl, COO—$C_{0-4}$alkylphenyl and COO—$C_{0-4}$alkylnaphthyl; and $R^{14}$ and $R^{15}$ are independently selected from the group consisting of:
  H and $C_{1-4}$alkyl.

3. A compound of claim 1, wherein:

A is phenyl, which is independently substituted with 0–2 $R^1$ substituents;

$R^1$ is selected from the group consisting of:
  halo, $(CH_2)_m NR^2 R^3$, $SO_2 NR^2 R^3$ and $SO_2 R^2$;

$R^2$ and $R^3$ are independently selected from the group consisting of:
  H and $C_{1-4}$alkyl;

Y is a direct link;

D is a phenyl, which is independently substituted with 0–2 $R^{1a}$ substituents;

$R^{1a}$ is selected from the group consisting of:
  Halo and $C_{1-4}$alkyl;

E is —N($R^5$)—C(=O)—;

$R^5$ is selected from the group consisting of:
  H, $C_{1-4}$alkyl, $C_{0-4}$alkylphenyl, $C_{0-4}$alkylnaphthyl and $C_{0-4}$alkylheteroaryl;

G is selected from the group consisting of:
  —$CR^7 R^8$— and —$CR^{7a} R^{8a}$—$CR^{7b} R^{8b}$— wherein $R^7$, $R^8$, $R^{7a}$, $R^{8a}$, $R^{7b}$ and $R^{8b}$ are independently a member selected from the group consisting of:
  hydrogen, $C_{1-4}$alkyl, $C_{0-4}$alkyl-$C_{3-8}$cycloalkyl, $C_{0-4}$alkylphenyl, $C_{0-4}$alkylnaphthyl, —$C_{0-4}$alkylCOO$R^9$, —$OR^9$, —$C_{0-4}$alkylC(=O) N$R^9 R^{10}$, —$C_{0-4}$alkylC(=O)N$R^9$—$CH_2$—$CH_2$—O—$R^{10}$, —$C_{0-4}$alkylC(=O)N$R^9$(—$CH_2$—$CH_2$—O—$R^{10}$—)$_2$, —N($R^9$)CO$R^{10}$, —N($R^9$)C(=O)$R^{10}$, —N($R^9$)$SO_2 R^{10}$, and common amino acid side chains;

$R^9$ and $R^{10}$ are independently selected from the group consisting of:
  H and $C_{1-4}$alkyl, wherein the N$R^9 R^{10}$ group of $R^7$, $R^8$, $R^{7a}$, $R^{8a}$, $R^{7b}$ and $R^{8b}$ is optionally cyclized to form a 5–8 membered heterocyclic group;

J is —O—;

Z is a phenyl, which is independently substituted with 0–2 $R^{1b}$ substituents;

$R^{1b}$ is selected from the group consisting of:
  halo, $C_{1-4}$alkyl, OH, OBn, O—$CH_2$—$CH_2$—OH, O—$CH_2$—$CH_2$—O$CH_3$, O—$CH_2$—COOH, O—$CH_2$—C(=O)—O—$CH_3$, $NH_2$, NH—$CH_2$—$CH_2$—O—$CH_3$, NH—C(=O)—O—$CH_3$ and NH—$SO_2$—$CH_3$;

L is C(=$NR^{12}$)$NR^{12} R^{13}$; and $R^{12}$ and $R^{13}$ are independently selected from the group consisting of:
  hydrogen and $C_{1-4}$alkyl.

4. A compound of claim 1, wherein:

A is a member selected from the group consisting of:

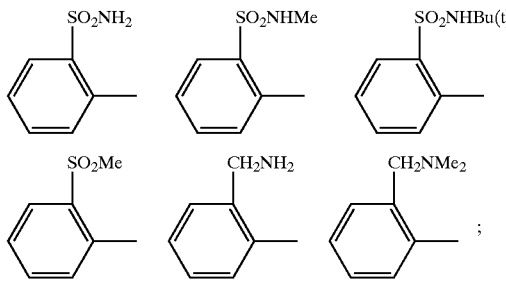

Y is a direct link;

D is a member selected from the group consisting of:

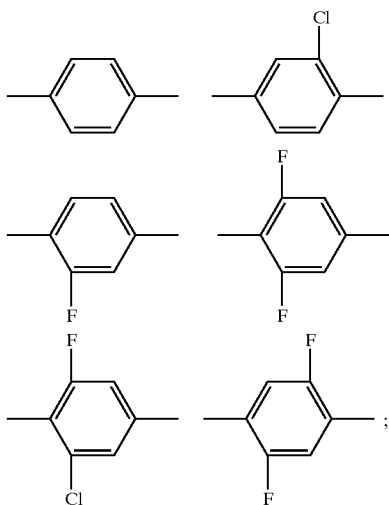

E is —NH—C(=O)—;

G is selected from the group consisting of:
—CH—(—NH$_2$)—CH$_2$—, —CH—(—NH(C(=O)—CH$_3$))—CH$_2$—, —CH—(—NH(C(=O)—Ph))—CH$_2$—, —CH—(C(=O)—OR$^8$)—, —CH(—R$^7$)—, —CH$_2$—CH(C(=O)—OR$^8$)—, and —CH$_2$—CH(C(=O)—N(—R$^8$, —R$^8$))—;

R$^7$ is a member selected from the group consisting of:
H, phenyl, Bn, —O-loweralkyl, and cyclohexyl;

R$^8$ is a member selected from the group consisting of:
H, C$_{1-6}$alkyl, —O-loweralkyl and C$_{3-6}$cycloalkyl;

J is —O—;

Z is a member selected from the group consisting of

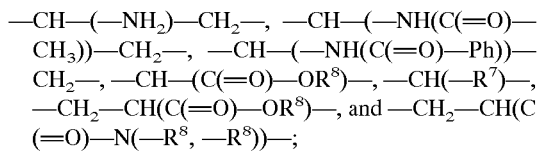

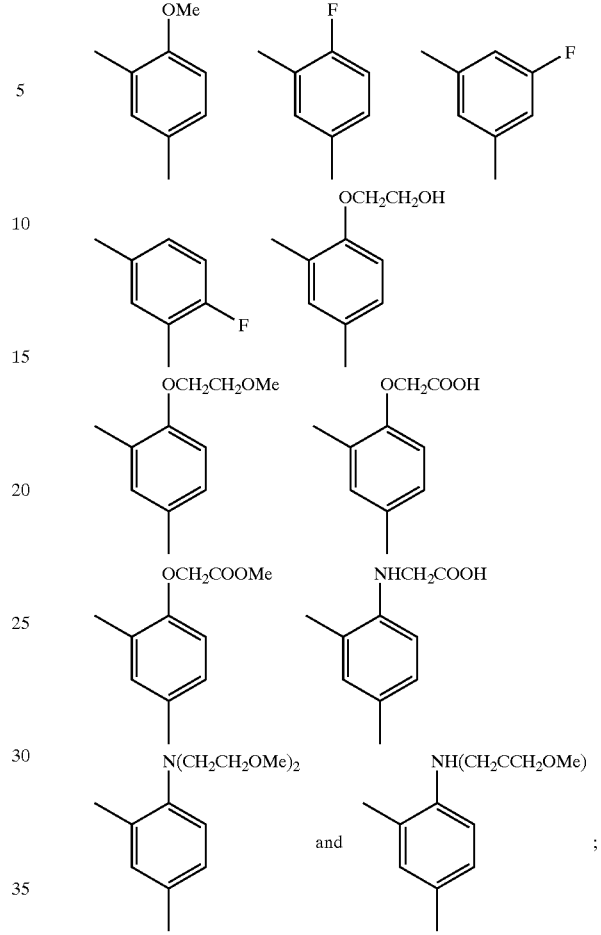

and L is —C(=NH)—NH$_2$.

5. A pharmaceutical composition for preventing or treating a condition in a mammal having undesired thrombosis comprising a pharmaceutically acceptable carrier and a compound of claim 1.

6. A pharmaceutical composition for preventing or treating a condition in a mammal having undesired thrombosis comprising a pharmaceutically acceptable carrier and a compound of claim 2.

7. A pharmaceutical composition for preventing or treating a condition in a mammal having undesired thrombosis comprising a pharmaceutically acceptable carrier and a compound of claim 3.

8. A pharmaceutical composition for preventing or treating a condition in a mammal having undesired thrombosis comprising a pharmaceutically acceptable carrier and a compound of claim 4.

9. A method for preventing or treating a condition in a mammal having undesired thrombosis comprising the step of administering to said mammal a therapeutically effective amount of a compound of claim 1.

10. The method of claim 9, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

11. A method for preventing or treating a condition in a mammal having undesired thrombosis comprising the step of administering to said mammal a therapeutically effective amount of a compound of claim 2.

12. The method of claim 11, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

13. A method for preventing or treating a condition in a mammal having undesired thrombosis comprising the step of administering to said mammal a therapeutically effective amount of a compound of claim 3.

14. The method of claim 13, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

15. A method for preventing or treating a condition in a mammal having undesired thrombosis comprising the step of administering to said mammal a therapeutically effective amount of a compound of claim 4.

16. The method of claim 15, wherein the condition is selected from the group consisting of: acute coronary syndrome, myocardial infarction, unstable angina, refractory angina, occlusive coronary thrombus occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolus, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, and conditions requiring the fitting of prosthetic devices.

17. A method for inhibiting the coagulation of biological samples comprising the step of administering to a mammal a therapeutically effective amount of a compound of claim 1.

18. A method for inhibiting the coagulation of biological samples comprising the step of administering to a mammal a therapeutically effective amount of a compound of claim 2.

19. A method for inhibiting the coagulation of biological samples comprising the step of administering to a mammal a therapeutically effective amount of a compound of claim 3.

20. A method for inhibiting the coagulation of biological samples comprising the step of administering to a mammal a therapeutically effective amount of a compound of claim 4.

* * * * *